(12) United States Patent
Krueger et al.

(10) Patent No.: US 7,358,282 B2
(45) Date of Patent: *Apr. 15, 2008

(54) LOW-DENSITY, OPEN-CELL, SOFT, FLEXIBLE, THERMOPLASTIC, ABSORBENT FOAM AND METHOD OF MAKING FOAM

(75) Inventors: Jeffrey Jennings Krueger, Marietta, GA (US); Fred Robert Radwanski, Stone Mountain, GA (US); Mark G. Reichmann, Roswell, GA (US); Peter Robert Elliker, Appleton, WI (US); Ali Yahiaoui, Roswell, GA (US); Renette E. Richard, Dunwoody, GA (US); Oomman Painummoottil Thomas, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 413 days.

This patent is subject to a terminal disclaimer.

(21) Appl. No.: 10/729,881

(22) Filed: Dec. 5, 2003

(65) Prior Publication Data

US 2005/0124709 A1 Jun. 9, 2005

(51) Int. Cl.
*C08J 9/00* (2006.01)
(52) U.S. Cl. .................. 521/81; 521/139; 521/140; 521/146; 521/148; 521/150
(58) Field of Classification Search ............. 521/81, 521/139, 140, 146, 148, 150
See application file for complete search history.

(56) References Cited

U.S. PATENT DOCUMENTS

| | | | |
|---|---|---|---|
| 3,432,449 A | 3/1969 | Deal et al. | |
| 3,563,243 A | 2/1971 | Lindquist | |
| 4,142,956 A | 3/1979 | Shikinami et al. | |
| 4,229,396 A | 10/1980 | Suh et al. | |
| 4,279,848 A | 7/1981 | Baxter et al. | |
| 4,306,035 A | 12/1981 | Baskent et al. | |
| 4,318,408 A | 3/1982 | Korpman | |
| 4,329,052 A | 5/1982 | Colombo et al. | |
| 4,343,911 A | 8/1982 | Hoki et al. | |
| 4,384,032 A | 5/1983 | Tashiro et al. | |
| 4,415,388 A | 11/1983 | Korpman | |
| 4,423,110 A | 12/1983 | Sato | |
| 4,435,346 A | 3/1984 | Ito et al. | |
| 4,449,977 A | 5/1984 | Korpman | |
| 4,519,963 A | 5/1985 | Yoshida et al. | |
| 4,554,297 A | 11/1985 | Dabi | |
| 4,560,372 A | 12/1985 | Pieniak | |
| 4,579,872 A | 4/1986 | Johnson | |
| 4,605,682 A | 8/1986 | Park | |
| 4,647,593 A | 3/1987 | Bartosiak et al. | |
| 4,655,210 A | 4/1987 | Edenbaum et al. | |
| 4,676,784 A | 6/1987 | Erdman et al. | |
| 4,725,629 A | 2/1988 | Garvey et al. | |
| 4,738,810 A | 4/1988 | Cheng-Shiang | |
| 4,747,983 A | 5/1988 | Colombo | |
| 4,762,860 A | 8/1988 | Park | |
| 4,766,157 A | 8/1988 | Yamada et al. | |
| 4,867,923 A | 9/1989 | Topcik et al. | |
| 4,894,395 A | 1/1990 | Park | |
| 4,902,565 A | 2/1990 | Brook | |
| 4,918,112 A | 4/1990 | Roox | |
| 5,019,062 A | 5/1991 | Ryan et al. | |
| 5,110,843 A | 5/1992 | Bries et al. | |
| 5,116,662 A | 5/1992 | Morman | |
| 5,116,881 A | 5/1992 | Park et al. | |
| 5,132,171 A | 7/1992 | Yoshizawa et al. | |
| 5,133,917 A | 7/1992 | Jezic et al. | |
| 5,147,338 A | 9/1992 | Lang et al. | |
| 5,147,345 A | 9/1992 | Young et al. | |
| 5,158,986 A | 10/1992 | Cha et al. | |
| 5,180,751 A | 1/1993 | Park et al. | |
| 5,188,885 A | 2/1993 | Timmons et al. | |
| 5,203,764 A | 4/1993 | Libbey et al. | |
| 5,204,174 A | 4/1993 | Daponte et al. | |
| 5,218,006 A | 6/1993 | Reedy et al. | |
| 5,244,931 A | 9/1993 | Kuyzin | |
| 5,250,577 A | 10/1993 | Welsh | |

(Continued)

FOREIGN PATENT DOCUMENTS

CA 2129278 2/1995

(Continued)

OTHER PUBLICATIONS

Landrock, Handbook of Plastic Foams, William Andrew Publishing, 1995, p. 308*

(Continued)

*Primary Examiner*—Irina S. Zemel
(74) *Attorney, Agent, or Firm*—Pauley Petersen & Erickson

(57) ABSTRACT

A soft, flexible, low-density, open-cell, thermoplastic, absorbent foam formed from a foam polymer formula including a balanced amount of a plasticizing agent and a surfactant in combination with a base resin. Thermoplastic elastomers can be added to the foam polymer formula to improve softness, flexibility, elasticity, and resiliency of the resulting foam. The surfactant may be either a single surfactant or a multi-surfactant system. The foam possesses a number of qualities, such as softness and strength, which render the foam particularly suitable for use in a variety of personal care products, medical products, and the like.

33 Claims, 10 Drawing Sheets

U.S. PATENT DOCUMENTS

| | | | |
|---|---|---|---|
| 5,268,224 A | 12/1993 | DesMarais et al. |
| 5,269,987 A | 12/1993 | Reedy et al. |
| 5,277,915 A | 1/1994 | Provonchee et al. |
| 5,286,429 A | 2/1994 | Blythe et al. |
| 5,290,822 A | 3/1994 | Rogers et al. |
| 5,294,482 A | 3/1994 | Gessner |
| 5,302,624 A | 4/1994 | Reedy et al. |
| 5,318,735 A | 6/1994 | Kozulla |
| 5,328,935 A | 7/1994 | Van Pahn et al. |
| 5,331,015 A | 7/1994 | DesMarais et al. |
| 5,342,857 A | 8/1994 | Reedy et al. |
| 5,348,795 A | 9/1994 | Park |
| 5,352,711 A | 10/1994 | DesMarais |
| 5,356,944 A | 10/1994 | Blythe et al. |
| 5,366,786 A | 11/1994 | Connor |
| 5,387,207 A | 2/1995 | Dyer et al. |
| 5,389,168 A | 2/1995 | Litchholt et al. |
| 5,403,865 A | 4/1995 | Reedy et al. |
| 5,405,883 A | 4/1995 | Park |
| 5,433,112 A | 7/1995 | Piche et al. |
| 5,460,818 A | 10/1995 | Park et al. |
| 5,489,407 A | 2/1996 | Suh et al. |
| 5,496,864 A | 3/1996 | Henn et al. |
| 5,534,335 A | 7/1996 | Everhart et al. |
| 5,536,264 A | 7/1996 | Hsueh et al. |
| 5,536,563 A | 7/1996 | Shah et al. |
| 5,550,167 A | 8/1996 | DesMarais |
| 5,567,742 A | 10/1996 | Park |
| 5,573,994 A | 11/1996 | Kabra et al. |
| 5,585,411 A | 12/1996 | Hwo |
| 5,589,519 A | 12/1996 | Knaus |
| 5,595,694 A | 1/1997 | Reedy et al. |
| 5,618,853 A | 4/1997 | Vonken et al. |
| 5,646,194 A | 7/1997 | Kobayashi et al. |
| 5,652,277 A * | 7/1997 | Reedy et al. ................. 521/91 |
| 5,674,916 A | 10/1997 | Schmidt et al. |
| 5,707,571 A | 1/1998 | Reedy |
| 5,728,406 A | 3/1998 | Halberstadt et al. |
| 5,744,506 A | 4/1998 | Goldman et al. |
| 5,763,067 A | 6/1998 | Brüggemann et al. |
| 5,767,189 A | 6/1998 | Palmer, Jr. |
| 5,770,634 A | 6/1998 | Dyer et al. |
| 5,788,889 A | 8/1998 | Demello et al. |
| 5,795,346 A | 8/1998 | Achter |
| 5,817,261 A | 10/1998 | Reedy et al. |
| 5,849,805 A | 12/1998 | Dyer |
| 5,855,572 A | 1/1999 | Schmidt |
| 5,880,166 A | 3/1999 | Glück et al. |
| 5,883,144 A | 3/1999 | Bambara et al. |
| 5,883,145 A | 3/1999 | Hurley et al. |
| 5,891,814 A | 4/1999 | Richeson et al. |
| 5,905,097 A | 5/1999 | Walther |
| 5,922,780 A | 7/1999 | Dyer et al. |
| 5,929,129 A | 7/1999 | Feichtinger |
| 5,962,543 A | 10/1999 | Kawasaki et al. |
| 5,962,545 A | 10/1999 | Chaudhary et al. |
| 5,993,706 A | 11/1999 | Wilkes et al. |
| 6,008,262 A | 12/1999 | McKay et al. |
| 6,027,795 A | 2/2000 | Kabra et al. |
| 6,030,696 A | 2/2000 | Lee |
| 6,051,174 A | 4/2000 | Park et al. |
| 6,071,580 A | 6/2000 | Bland et al. |
| 6,083,211 A | 7/2000 | DesMarais |
| 6,093,751 A | 7/2000 | Federico et al. |
| 6,093,752 A | 7/2000 | Park et al. |
| 6,096,793 A | 8/2000 | Lee et al. |
| 6,103,358 A | 8/2000 | Brüggemann et al. |
| 6,107,538 A | 8/2000 | Young et al. |
| 6,132,077 A | 10/2000 | Fogarty |
| 6,140,550 A | 10/2000 | Beihoffer et al. |
| 6,156,813 A | 12/2000 | Malwitz et al. |
| 6,174,471 B1 | 1/2001 | Park et al. |
| 6,197,233 B1 | 3/2001 | Mason et al. |
| 6,197,841 B1 | 3/2001 | Takimoto et al. |
| 6,221,928 B1 | 4/2001 | Kozma et al. |
| 6,231,960 B1 | 5/2001 | Dyer et al. |
| 6,235,360 B1 | 5/2001 | Lanzani et al. |
| 6,245,697 B1 | 6/2001 | Conrad et al. |
| 6,258,863 B1 | 7/2001 | Harfmann et al. |
| 6,258,868 B1 | 7/2001 | Heymann |
| 6,261,679 B1 | 7/2001 | Chen et al. |
| 6,262,137 B1 | 7/2001 | Kozma et al. |
| 6,268,046 B1 | 7/2001 | Miller et al. |
| 6,281,289 B1 | 8/2001 | Maugans et al. |
| 6,297,326 B1 | 10/2001 | Wang et al. |
| 6,310,112 B1 | 10/2001 | Vo et al. |
| 6,325,956 B2 | 12/2001 | Chaudhary et al. |
| 6,329,450 B1 | 12/2001 | Ogoe et al. |
| 6,355,341 B1 | 3/2002 | Chaudhary et al. |
| 6,372,953 B1 | 4/2002 | Young et al. |
| 6,376,565 B1 | 4/2002 | Dyer et al. |
| 6,388,014 B1 | 5/2002 | Park et al. |
| 6,391,438 B1 | 5/2002 | Ramesh et al. |
| 6,398,997 B1 | 6/2002 | Ligon, Sr. et al. |
| 6,399,854 B1 | 6/2002 | Vartianen |
| 6,414,047 B1 | 7/2002 | Abe |
| 6,417,240 B1 | 7/2002 | Park |
| 6,436,521 B1 | 8/2002 | Lee |
| 6,451,865 B1 | 9/2002 | Migchels et al. |
| 6,458,877 B1 | 10/2002 | Ahmed et al. |
| 6,605,332 B2 | 8/2003 | Calhoun et al. |
| 6,638,985 B2 | 10/2003 | Gehlsen et al. |
| 6,653,360 B2 | 11/2003 | Gupta |
| 2002/0010270 A1 | 1/2002 | Czech et al. |
| 2002/0025988 A1 | 2/2002 | Maekawa et al. |
| 2002/0197442 A1 | 12/2002 | Wyner et al. |
| 2004/0005434 A1 | 1/2004 | Calhoun et al. |
| 2005/0124709 A1 | 6/2005 | Krueger et al. |

FOREIGN PATENT DOCUMENTS

| | | |
|---|---|---|
| EP | 0 041 934 | 12/1981 |
| EP | 0 043 052 | 1/1982 |
| EP | 0 228 353 B1 | 5/1991 |
| EP | 0 328 518 B1 | 5/1991 |
| EP | 0 453 286 A2 | 10/1991 |
| EP | 0 475 174 B1 | 5/1996 |
| EP | 0 517 748 B1 | 12/1996 |
| EP | 0 753 529 A2 | 1/1997 |
| EP | 0 642 907 B1 | 5/1997 |
| EP | 0 585 147 B1 | 4/1998 |
| EP | 0 878 481 A1 | 11/1998 |
| EP | 0 921 148 A1 | 6/1999 |
| EP | 0 674 579 B1 | 6/2000 |
| EP | 0 662 493 B1 | 10/2000 |
| EP | 0 753 529 A3 | 11/2000 |
| EP | 1 048 276 A1 | 11/2000 |
| EP | 1 054 033 A1 | 11/2000 |
| EP | 1 115 777 B1 | 7/2001 |
| EP | 0 891 390 B1 | 8/2001 |
| EP | 0 704 476 B1 | 12/2001 |
| EP | 1 182 224 A1 | 2/2002 |
| EP | 1 219 673 A2 | 7/2002 |
| EP | 1 219 673 A3 | 7/2002 |
| EP | 1 079 786 B1 | 8/2002 |
| EP | 0 702 032 B1 | 11/2002 |
| EP | 0 975 696 B1 | 6/2003 |
| GB | 2 259 464 A | 3/1993 |
| GB | 2 279 013 A | 12/1994 |
| JP | 4-46981 | 7/1992 |
| JP | 6-280317 | 10/1994 |
| JP | 2001-342277 | 12/2001 |
| WO | WO86/00628 | 1/1986 |
| WO | WO91/08037 | 6/1991 |

| | | |
|---|---|---|
| WO | WO94/13460 | 6/1994 |
| WO | WO97/07907 | 3/1997 |
| WO | WO97/11985 | 4/1997 |
| WO | WO97/31053 | 8/1997 |
| WO | WO98/10015 | 3/1998 |
| WO | WO98/14508 | 4/1998 |
| WO | WO98/16575 | 4/1998 |
| WO | WO98/37131 | 8/1998 |
| WO | WO98/41574 | 9/1998 |
| WO | WO98/58991 | 12/1998 |
| WO | WO99/00236 | 1/1999 |
| WO | WO99/29765 | 6/1999 |
| WO | WO99/47092 | 9/1999 |
| WO | WO99/47592 | 9/1999 |
| WO | WO99/52955 | 10/1999 |
| WO | WO 00/15697 | 3/2000 |
| WO | WO 00/15700 | 3/2000 |
| WO | WO 00/53669 | 3/2000 |
| WO | WO 01/09239 A1 | 2/2001 |
| WO | WO 01/15643 A1 | 3/2001 |
| WO | WO 01/16220 A1 | 3/2001 |
| WO | WO 01/21227 A1 | 3/2001 |
| WO | WO 01/27191 A1 | 4/2001 |
| WO | WO 01/34687 A1 | 5/2001 |
| WO | WO 01/40374 A2 | 6/2001 |
| WO | WO 01/40374 A3 | 6/2001 |
| WO | WO 01/64154 A1 | 9/2001 |
| WO | WO 01/70479 A1 | 9/2001 |
| WO | WO 01/70859 A2 | 9/2001 |
| WO | WO 01/70859 A3 | 9/2001 |
| WO | WO 01/70860 A2 | 9/2001 |
| WO | WO 01/70860 A3 | 9/2001 |
| WO | WO 01/80916 A2 | 11/2001 |
| WO | WO 01/80916 A3 | 11/2001 |
| WO | WO 02/07791 A2 | 1/2002 |
| WO | WO 02/07791 A3 | 1/2002 |
| WO | WO 02/12379 A1 | 2/2002 |
| WO | WO 02/14424 A2 | 2/2002 |
| WO | WO 02/18482 A2 | 3/2002 |
| WO | WO 02/22339 A1 | 3/2002 |
| WO | WO 02/34823 A2 | 5/2002 |
| WO | WO 02/068530 A2 | 9/2002 |

OTHER PUBLICATIONS

Rynel EPITECH® brochure, 1997.
Jeffrey Csemica and Alisha Brown, "Effect of Plasticizers on the Properties of Polystyrene Films", Journal of Chemical Education, vol. 76, No. 11, Nov. 1999, pp. 1526-1528.
"Kraton D and G Polymers," www. Kraton.com/kraton/generic/menu.asp?ID=220, Oct. 2001.
Epolene® Polymers brochure, Eastman Chemical Company, 2002, pp. 9, 11, 12.
"Epolene Polymers", www.eastman.com/Brands/Epolene/Epolene_Intro.asp, 2003.
"Epolene Polymers", www.eastman.com/Online_Publication/F243/P24304.htm, 1994.
"Epolene Polymers: Effective Processing Aids for Rubber," Eastman Chemical Company, Aug. 1995, pp. 1-8.
"Glycerol Monooleate: Processing," National Organic Standards Board Technical Advisory Panel Review, Sep. 2001, pp. 1-16.
Principles of Polymer Systems, Ferdinand Rodriquez, McGraw-Hill Book Co., 1070, pp. 43-46.

* cited by examiner

Sample 1c

Sample 3c

Sample 4c

Sample 6c

Sample 7c

Sample 8c

Sample 9c

Sample 10c

Sample 11c

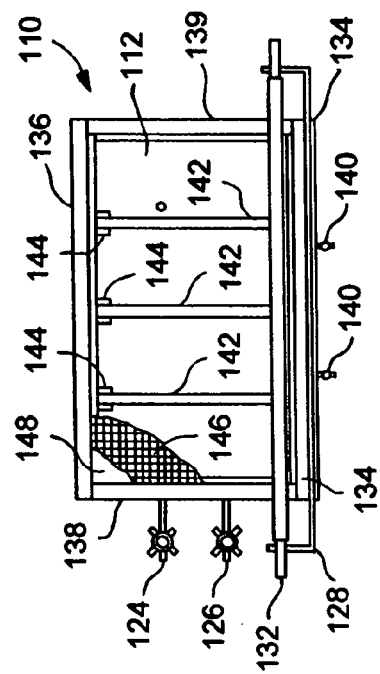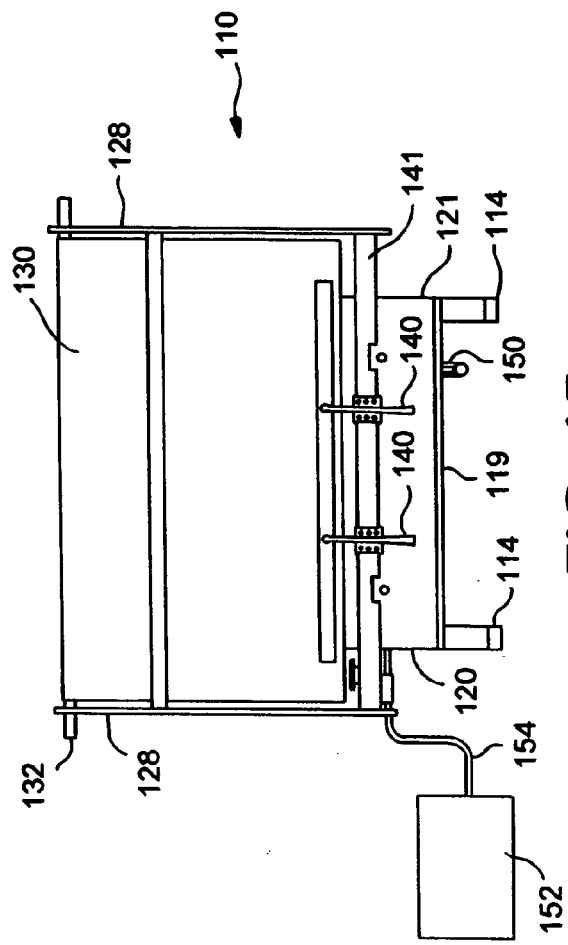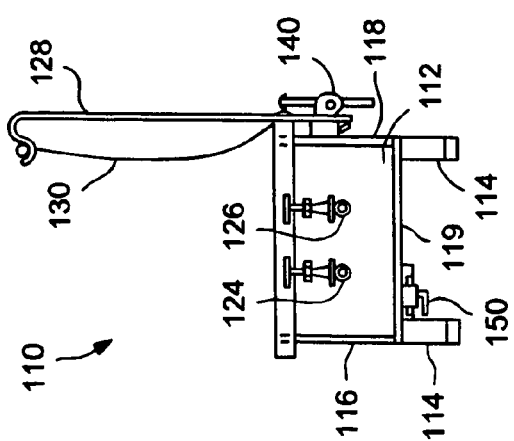

LOW-DENSITY, OPEN-CELL, SOFT, FLEXIBLE, THERMOPLASTIC, ABSORBENT FOAM AND METHOD OF MAKING FOAM

BACKGROUND OF THE INVENTION

This invention is directed to a low-density, open-cell, thermoplastic, absorbent foam that is soft and flexible. The foam can be made with balanced amounts of one or more surfactants and a plasticizing agent in a foam polymer formula. Thermoplastic elastomers can be added to the foam polymer formula to improve softness, flexibility, elasticity and resiliency.

Thermoplastic absorbent foam is made of polymer(s) that can be heated, formed and cooled repeatedly, typically commercially using a continuous plastic extrusion process. Thermoplastic absorbent foam can be used to produce personal care products including, but not limited to, absorbent articles such as disposable diapers, baby wipes, training pants, child-care pants, and other disposable garments; feminine-care products including, but not limited to, sanitary napkins, wipes, menstrual pads, panty liners, panty shields, tampons, and tampon applicators; adult-care products including, but not limited to, wipes, pads, containers, incontinence products, and urinary shields. Besides use of such foam for personal care products, thermoplastic absorbent foam can also be used in a wide array of applications including a variety of professional and consumer health and medical care products including, but not limited to, products for applying hot or cold therapy, hospital gowns, surgical drapes, bandages, wound dressings, wipes, covers, containers, filters, disposable garments and bed pads, medical absorbent garments, underpads, and the like, as well as clothing components, filters, thermal and acoustic insulation, shock and cushion absorbing products, athletic and recreation products, construction and packaging uses, and service, industrial, and household products including, but not limited to, cleaning applications such as sponges and wipes for oleophilic and/or hydrophilic fluids; products for cleaning and disinfecting, and covers, filters, towels, bath tissue, and facial tissue; nonwoven roll goods; home-comfort products including pillows, pads, cushions, and masks and body-care products such as washcloths, and products used to cleanse or treat the skin. Low foam density and low modulus are required for high absorbency, softness, flexibility, and in desired hand and fit aesthetics for applications such as diapers, incontinence products, and other aforementioned products.

Extruded foams have a cellular structure, with cells defined by cell membranes and struts. Struts are formed at the intersection of cell membranes, with the cell membranes covering interconnecting cellular windows between the struts. The thickness of cell struts is typically 2–10 times greater than the thickness of cell membranes. Extruded foams are typically produced with substantially closed cells. The open-cell content of closed-cell foams is generally less than 20%. Acceptable absorbent foam has an open-cell structure, typically 50% or higher, as measured by ASTM D2856, and suitably has a controlled cell diameter. Specific cell size and cellular connectivity are adjusted to the desired function, such as for high capillary fluid movement and high absorption capacity. Cell wall or membrane pores that connect cells are of sufficient number and size to minimize viscous drag and flow resistance to produce effective fluid transport and containment. Reticulated foam generally has a minimal number of cell windows or no cell windows (only struts) and, with sufficiently small enough pores, can effectively transport capillary fluid. Such open-pore structures lend themselves to rapid fluid intake.

Processes are known for making open-cell foams, low-density foams, absorbent foams, and soft, resilient, elastomeric foams. One process for enhancing the open-cell formation in foam is described, for example, in U.S. Pat. No. 5,962,545. All of these foam qualities in a single foam would be particularly desirable in a number of absorbent product applications; however, it is difficult to produce such foam.

Foaming soft, flexible polymers, such as thermoplastic elastomers, to low densities with absorbency is difficult to achieve. U.S. Pat. No. 5,728,406 describes low-density, flexible, non-absorbent foam. As described in U.S. Pat. No. 6,451,865, heat-expandable thermoplastic particles that encapsulate a heat-expandable gas or liquefied gas can be added to produce such thermoplastic elastomer foam.

Plasticizing agents are sometimes used as cell openers in producing foams. When used as cell openers, these plasticizing agents are added to the thermoplastic foam polymer formula in minor amounts, as described in U.S. Pat. No. 6,071,580. More particularly, the plasticizing agent can act to increase cell expansion to produce a high expansion ratio. When cells expand, membranes between cells thin and can become unstable, rupture, and can thereby create porous connections between cells. In addition, when thermoplastic polymer cools and with volumetric contraction with crystallization, thin portions of the membrane can rupture enough to create additional connections or pores between cells, thereby creating open cells.

Although plasticizing agents act as softeners, the addition of plasticizing agents makes foaming to low densities even more difficult. U.S. Pat. No. 6,653,360 describes a high density, essentially closed-cell, non-absorbing foam containing a plasticizing agent and thermoplastic elastomer and additive such as a surfactant. In particular, plasticizing agents typically lower polymer melt viscosities and lead to increasing melt drainage that causes foaming difficulties with cell collapse. In fact, in certain manufacturing processes, such as food packaging processes, plasticizing agents are used as defoaming agents.

There is a wide range of FDA-approved plasticizing agents available. The criterion for selecting a plasticizing agent for personal care products includes a wide range of properties including not only its softening ability but also temperature stability upon extrusion, resistance to migration, cost, odor, biodegradability, and manufacturing and consumer safety. Typical plasticizing agents include citrates, phthalates, stearates, fats and oils. It is known that glycerol fatty acids, such as glycerol monostearate, stabilize cells by reducing the rate of gas diffusion from the cell. However, such glycerol fatty acids are unable to provide sufficient wettability.

There is thus a need or desire for a soft, flexible, low-density, open-cell, thermoplastic, absorbent foam, and a method of making such foam.

SUMMARY OF THE INVENTION

This invention is directed to soft, flexible, low-density, open-cell, thermoplastic, absorbent foam, and a method of making such foam by forming a foam polymer formula that includes one or more surfactants and a plasticizing agent in combination with a base resin. Consequently, the foam of the invention can include one or more surfactants and a plasticizing agent in combination with a base resin. The amount of surfactant and/or plasticizing agent can be adjusted in order to control softness, open-cell content, and cellular size and structure of the resulting foam. Additionally, a thermoplastic elastomer can be added to the foam polymer formula in addition to, or in place of, the plasticizing agent to enhance the resiliency, flexibility, softness, and elasticity of the resulting foam.

The open-cell content of the foam is about 50% or greater. Additionally, the absorbent foam may have about 5% or more closed cells, or about 10% or more closed cells, or about 15% or more closed cells to improve resiliency and/or compression resistance. The foam is low density, with a density of about 0.1 gram/cubic centimeter ($g/cm^3$) or less, and is soft and flexible, with a Gurley stiffness of about 600 milligrams or less, and an edge compression of about 250 grams or less. As another measure of softness, flexibility, elasticity, and resiliency, the foam suitably has a compression resistance of about 20% compression set or less. The addition of the surfactant and plasticizing agent to the foam polymer formula also enhances the uniformity of cell distribution within the foam.

The foam is absorbent and remains suitably absorbent even after repeated washings. The surfactant permanence remains intact in the foam such that about 15% or less of the surfactant is washed off after soaking in water for 24 hours and, alternatively, the surface tension of the supernatant remains greater than about 40 dynes/centimeter, and with 0.9% NaCl saline has a saturated capacity of about 3 grams/gram or greater, as measured under a 0.5 psi loading, and a fluid intake flux of about 1 $ml/sec/in^2$ or greater upon the first insult, about 1 $ml/sec/in^2$ or greater upon the second insult, and about 1 $ml\ sec/in^2$ or greater upon the third insult. Furthermore, the foam suitably has a vertical wicking height of about 5 cm or higher in 30 minutes. With viscous fluid, saturation capacity is about 3 g/g or greater and retention capacity is about 1 g/g or greater.

The foam may be thin, but possesses considerable strength. More particularly, the foam may have a basis weight of about 400 grams per square meter or less, with an overall bulk, measured at a 0.02 psi loading, of about 6 millimeters or less, and a machine-direction (MD) and cross-direction (CD) trap tear strength each of about 300 grams or greater.

One method of making the foam includes formulating a foam polymer formula by including both a plasticizing agent and a surfactant in combination with a base resin, heating the foam polymer formula to create a polymer melt, utilizing a blowing agent, extruding the polymer melt, and foaming the polymer melt to a density of about 0.1 $g/cm^3$ or less, to form an open-cell, soft, flexible, thermoplastic, absorbent foam. Alternatively, rather than a single surfactant, a multi-component surfactant system can be included in the foam polymer formula. Unlike many foam-forming processes, the method of the invention is a non-aqueous method.

Suitably, the surfactant can be included in the foam polymer formula in an amount between about 0.05% and about 10%, by weight, of the foam polymer formula, and the plasticizing agent can be included in the foam polymer formula in an amount between about 0.5% and about 10%, by weight, of the foam polymer formula.

The plasticizing agent is typically used to increase flexibility and softness in rigid polymers and can also create open-cell structure in the resulting foam by increasing drainage. However, the addition of a plasticizing agent makes it more difficult to achieve low-density foam. According to this invention, it has been found that the addition of a surfactant enables foaming of a foam polymer formula to low densities, even when the foam polymer formula includes a plasticizing agent. The benefits derived from the use of a plasticizing agent in the low-density, open-cell foam-forming process are particularly unexpected. Chemicals used as plasticizing agents sometimes are used as defoaming agents. By adding surfactant(s) to the plasticizing agent, this invention counteracts the negative impact of such plasticizing/defoaming chemicals for use in a foam-forming process.

As mentioned, the open-cell content of the foam can be controlled by adjusting the amount of the surfactant and/or plasticizing agent in the foam polymer formula. More particularly, the balance between cell stabilization with the surfactant and enhanced drainage from the plasticizing agent enables control over the open-cell content. The surfactant also provides wettability to enable the resulting foam to absorb fluid. It has been shown that introduction of certain surfactants via various processes can lead to a highly substantive surfactant for continued wettability upon repeated washings. For example, use of HOSTASTAT® HS-1 and other surfactants have remained 95% (by weight) intact even after 24 hours of washing with water. Additionally, it has been found that a multi-component surfactant system can achieve equal or better foam formation at a lower dosage than a single-component surfactant system.

In certain embodiments, a thermoplastic elastomer can be included in the foam polymer formula to improve softness, flexibility, resiliency, and elasticity of the resulting foam.

With the foregoing in mind, it is a feature and advantage of the invention to provide a low-density, open-cell, thermoplastic, absorbent foam that is soft and flexible, and a method of making such a foam in which the open-cell content can be controlled.

BRIEF DESCRIPTION OF THE DRAWINGS

These and other objects and features of this invention will be better understood from the following detailed description taken in conjunction with the drawings, wherein:

FIG. 13 representatively shows a partially cut away top view of a saturated capacity tester.

FIG. 14 representatively shows a side view of a saturated capacity tester.

FIG. 15 representatively shows a rear view of a saturated capacity tester.

DEFINITIONS

Figure 1:
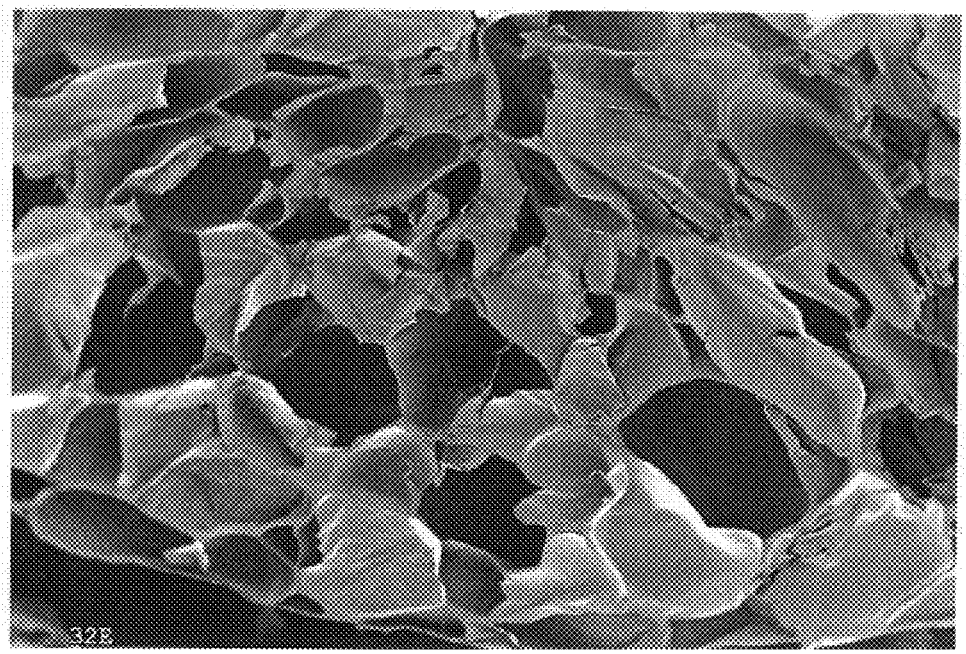
FIG. 1 is a photomicrograph of a cross-section of a foam, described in Example 1, taken by scanning electron microscopy. The photomicrograph was taken at a magnification of 15×.

Within the context of this specification, each term or phrase below will include the following meaning or meanings.

"Cell" refers to a cavity contained in foam. A cell is closed when the cell membrane surrounding the cavity or enclosed opening is not perforated and has all membranes intact. Cell connectivity occurs when at least one wall of the cell membrane surrounding the cavity has orifices or pores that connect to adjacent cells, such that an exchange of fluid is possible between adjacent cells.

"Compression" refers to the process or result of pressing by applying force on an object, thereby increasing the density of the object.

"Elastomer" refers to material having elastomeric or rubbery properties. Elastomeric materials, such as thermoplastic elastomers, are generally capable of recovering their shape after deformation when the deforming force is removed. Specifically, as used herein, elastomeric is meant to be that property of any material which upon application of an elongating force, permits that material to be stretchable to a stretched length which is at least about 25 percent greater than its relaxed length, and that will cause the material to recover at least 40 percent of its elongation upon release of the stretching elongating force. A hypothetical example which would satisfy this definition of an elastomeric material in the X-Y planar dimensions would be a one (1) inch sample of a material which is elongatable to at least 1.25 inches and which, upon being elongated to 1.25 inches and released, will recover to a length of not more than 1.15 inches. Many elastomeric materials may be stretched by much more than 25 percent of their relaxed length, and many of these will recover to substantially their original relaxed length upon release of the stretching, elongating force. In addition to a material being elastomeric in the described X-Y planar dimensions of a structure, including a web or sheet, the material can be elastomeric in the Z planar dimension. Specifically, when a structure is applied compression, it displays elastomeric properties and will essentially recover to its original position upon relaxation. Compression set is sometimes used to describe such elastic recovery.

"Open cell" refers to any cell that has at least one broken or missing membrane or a hole in a membrane.

"Plasticizing agent" refers to a chemical agent that can be added to a rigid polymer to add flexibility to rigid polymers. Plasticizing agents typically lower the glass transition temperature.

"Polymer" generally includes but is not limited to, homopolymers, copolymers, including block, graft, random and alternating copolymers, terpolymers, etc., and blends and modifications thereof. Furthermore, unless otherwise specifically limited, the term "polymer" shall include all possible molecular geometrical configurations of the material. These configurations include, but are not limited to isotactic, syndiotactic and atactic symmetries.

"Surfactant" is a compound, such as detergents and wetting agents, that affects the surface tension of fluids.

"Thermoplastic" is meant to describe a material that softens and/or flows when exposed to heat and which substantially returns to its original hardened condition when cooled to room temperature.

"Absorbent article" includes, but is not limited to, personal care absorbent articles, medical absorbent articles, absorbent wiping articles, as well as non-personal care absorbent articles including filters, masks, packaging absorbents, trash bags, stain removers, topical compositions, laundry soil/ink absorbers, detergent agglomerators, lipophilic fluid separators, cleaning devices, and the like.

"Personal care absorbent article" includes, but is not limited to, absorbent articles such as disposable diapers, baby wipes, training pants, child-care pants, and other disposable garments; feminine-care products including sanitary napkins, wipes, menstrual pads, panty liners, panty shields, interlabials, tampons, and tampon applicators; adult-care products including wipes, pads, containers, incontinence products, and urinary shields; and the like.

"Medical absorbent article" includes a variety of professional and consumer health-care products including, but not limited to, products for applying hot or cold therapy, hospital gowns, surgical drapes, bandages, wound dressings, covers, containers, filters, disposable garments and bed pads, medical absorbent garments, gowns, underpads, wipes, and the like.

"Absorbent wiping article" includes facial tissue, towels such as kitchen towels, disposable cutting sheets, away-from-home towels and wipers, wet-wipes, sponges, washcloths, bath tissue, and the like.

"Menses simulant" is a material that simulates the viscoelastic and other properties of menses, which is a "complex liquid." As used herein, the phrase "menses simulant" or "complex liquid" describes a liquid generally characterized as being a viscoelastic fluid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water, and the like, are generally characterized as having a relatively low viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others. Although a complex liquid is generally characterized herein as including specific components having inhomogeneous properties, each specific component of a complex liquid generally has homogeneous properties. Consider for example a representative complex body-liquid having three specific components: red blood cells, blood protein molecules, and water molecules. Upon examination, one skilled in the art could easily distinguish between each of the three specific components according to their generally inhomogeneous properties. Moreover, when examining a particular specific component, such as the red blood cell component, one skilled in the art could easily recognize the generally homogeneous properties of the red blood cells. The "menses simulant" test fluid used in this invention is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed.

"Viscous fluid" refers to a fluid having a viscosity greater than the viscosity of water, including such fluids as menses, menses simulant, fecal fluid, fecal fluid simulant, and the like.

These terms may be defined with additional language in the remaining portions of the specification.

DESCRIPTION OF PREFERRED EMBODIMENTS

In accordance with the invention, a soft, flexible, low-density, open-cell, thermoplastic, absorbent foam can be made by forming a foam polymer formula that includes a plasticizing agent and one or more surfactants in combination with a base resin. The plasticizing agent included in the foam polymer formula may further increase the softness of the resulting foam and, optionally, to increase the open-cell content and cell size of the resulting foam.

The foam of the invention possesses a number of desirable properties attributable to the balanced presence of both a plasticizing agent and surfactant. The inclusion of the surfactant and plasticizing agent in the foam polymer formula enhances softness, flexibility, absorbency, as well as the uniformity of cell-size distribution within the foam. As used herein, the term "foam polymer formula" refers to the composition of the foam during the foam-forming process, whereas the term "foam" refers to a finished or formed state of the foam. The composition of the foam is considered to be generally equivalent to the composition of the foam polymer formula.

The soft, flexible, low-density, open-cell, thermoplastic, absorbent foam is particularly suitable for use in a variety of absorbent article applications including, without limitation, personal care absorbent articles, medical absorbent articles, and absorbent wiping articles. Personal care absorbent articles include, but are not limited to, absorbent articles such as disposable diapers, baby wipes, training pants, child-care pants, swimwear, and other disposable garments; feminine-care products including, but not limited to, sanitary napkins, wipes, menstrual pads, panty liners, panty shields, interlabials, tampons, and tampon applicators; adult-care products including, but not limited to, wipes, pads, containers, incontinence products, and urinary shields. Medical absorbent articles include professional and consumer health medical care products such as products for applying hot or cold therapy, hospital gowns, surgical drapes, bandages, wound dressings, wipes, covers, containers, filters, disposable garments and bed pads, medical absorbent garments, underpads, and the like. Absorbent wiping articles include facial tissue, washcloths, cleaning applications including sponges and wipes and impregnated wipes, towels such as kitchen towels, disposable cutting sheets, away-from-home towels, wet-wipes, bath tissue, and the like. Besides use of such foam for personal care products, the foam can also be used in a wide array of applications including a variety of clothing components, and non-personal care absorbent products including filters, masks, packaging absorbents, trash bags, stain removers, topical compositions, laundry soil/link absorbers, detergent agglomerators, lipophilic fluid separators, cleaning devices, athletic and recreation products, and construction and packaging uses. Additionally, because the foam is thermoplastic, the foam is also recyclable.

The open-cell content of the foam, which can be controlled by adjusting the amount of surfactant and/or plasticizing agent included in the foam polymer formula, is suitably about 50% or greater, or about 70% or greater, or about 80% or greater, as measured using ASTM D2856. The foam is low density, with a density of about 0.1 gram/cubic centimeter ($g/cm^3$) or less, or about 0.05 $g/cm^3$ or less, or about 0.01 $g/cm^3$ or less (before any compression is applied to meet specific packaging and/or in-use requirements), and is soft and flexible, with a Gurley stiffness of about 600 milligrams or less, or about 300 milligrams or less, or about 150 milligrams or less, or about 50 milligrams or less; and is resilient and elastic with an edge compression of about 250 grams or less, or about 100 grams or less, or about 35 grams or less. Gurley stiffness can be measured using the Gurley Stiffness Test Method, and edge compression can be measured using the Edge Compression Test Method, both of which are described in detail below. Softness, flexibility, elasticity, and resiliency are also demonstrated through compression set resistance. The foam of the invention suitably has a compression resistance of about 20% compression set or less, or about 15% compression set or less, or about 7% compression set or less, as measured using ASTM D3575.

The foam remains suitably absorbent even after repeated washings. The surfactant permanence remains intact in the foam such that about 15% or less, or about 10% or less, or about 5% or less of the surfactant is washed off after soaking in water for 24 hours. The Surfactant Permanence Test is described in detail below. An alternative measure of the surfactant permanence is the surface tension of the supernatant in the same Surfactant Permanence Test. More particularly, the surface tension remains greater than about 40 dynes/centimeter, or greater than about 50 dynes/centimeter, or greater than about 60 dynes/centimeter.

The absorbent foam with 0.9% NaCl saline has a saturated capacity of about 3 grams/gram (g/g) or greater, or about 15 g/g or greater, or about 30 g/g or greater, or about 100 g/g or greater, as measured under a 0.5 psi load using the Saturated Capacity Test Method, described in detail below, and a fluid intake flux of about 1 ml/sec/in$^2$ or greater, or about 3 ml/sec/in$^2$ or greater, or about 5 ml/sec/in$^2$ or greater upon the first insult, about 1 ml/sec/in$^2$ or greater, or about 3 ml/sec/in$^2$ or greater, or about 5 ml/sec/in$^2$ or greater upon the second insult, and about 1 ml/sec/in$^2$ or greater, or about 3 ml/sec/in$^2$ or greater, or about 5 ml/sec/in$^2$ or greater upon the third insult, using the Fluid Intake Flux Test or Modified Fluid Intake Flux Test, also described in detail below. Furthermore, the foam has a vertical wicking height of about 5 centimeters (cm) or higher, or about 7 cm or higher, or about 10 cm or higher, or about 15 cm or higher in 30 minutes, as measured with 0.9% NaCl saline solution using the Vertical Wicking Test, also described in detail below. With viscous fluid, saturation capacity is about 3 g/g or greater, or about 25 μg or greater, or about 100 g/g or greater, and retention capacity is about 1 g/g or greater, or about 3 μg or greater, or about 8 g/g or greater as determined using the Viscous Fluid Saturation Capacity and Retention Capacity Test, also described in detail below.

The thermoplastic absorbent foam may be thin, but possesses considerable strength. More particularly, the foam may have a basis weight of about 400 grams per square meter or less, with an overall bulk, measured at 0.02 psi loading, of about 6 millimeters or less. Suitably, the foam has a cross-direction (CD) trap tear strength of about 300 grams or greater, or about 600 grams or greater, or about 1200 grams or greater, and a machine-direction (MD) trap tear strength of about 300 grams or greater, or about 600 grams or greater, or about 1200 grams or greater. Overall bulk can be measured using a hand micrometer, while avoiding surface compression. Trap tear MD/CD strength of the foam may be measured using ASTM D1117-14.

Any one or more of the foam properties disclosed herein may be present in the foam of the invention.

The base resin, or starting material, included in the foam polymer formula used to make the foam of the invention can include any suitable thermoplastic polymer, or blend of thermoplastic polymers, or blend of thermoplastic and non-thermoplastic polymers.

Examples of polymers, or base resins, suitable for use in the foam polymer formula include styrene polymers, such as polystyrene or polystyrene copolymers or other alkenyl aromatic polymers; polyolefins including homo or copolymers of olefins, such as polyethylene, polypropylene, polybutylene, etc.; polyesters, such as polyalkylene terephthalate; and combinations thereof. A commercially available example of polystyrene resin is Dow STYRON® 685D, available from Dow Chemical Company in Midland, Mich., U.S.A.

Coagents and compatibilizers can be utilized for blending such resins. Crosslinking agents can also be employed to enhance mechanical properties, foamability and expansion. Crosslinking may be done by several means including electron beams or by chemical crosslinking agents including organic peroxides. Use of polymer side groups, incorporation of chains within the polymer structure to prevent polymer crystallization, lowering of the glass transition temperature, lowering a given polymer's molecular weight distribution, adjusting melt flow strength and viscous elastic properties including elongational viscosity of the polymer melt, block copolymerization, blending polymers, and use of polyolefin homopolymers and copolymers have all been used to improve foam flexibility and foamability. Homopolymers can be engineered with elastic and crystalline areas. Syndiotactic, atactic and isotactic polypropylenes, blends of such and other polymers can also be utilized. Suitable polyolefin resins include low, including linear low, medium and high-density polyethylene and polypropylene, which are normally made using Ziegler-Natta or Phillips catalysts and are relatively linear; generally more foamable are resins having branched polymer chains. Isotactic propylene homopolymers and blends are made using metallocene-based catalysts. Olefin elastomers are included.

Ethylene and α-olefin copolymers, made using either Ziegler-Natta or a metallocene catalyst, can produce soft, flexible foam having extensibility. Polyethylene crosslinked with α-olefins and various ethylene ionomer resins can also be utilized. Use of ethyl-vinyl acetate copolymers with other polyolefin-type resins can produce soft foam. Common modifiers for various polymers can also be reacted with chain groups to obtain suitable functionality. Suitable alkenyl aromatic polymers include alkenyl aromatic homopolymers and copolymers of alkenyl aromatic compounds and copolymerizable ethylenically unsaturated comonomers including minor proportions of non-alkenyl aromatic polymers and blends of such. Ionomer resins can also be utilized.

Other polymers that may be employed include natural and synthetic organic polymers including cellulosic polymers, methyl cellulose, polylactic acids, polyvinyl acids, polyacrylates, polycarbonates, starch-based polymers, polyetherimides, polyamides, polyesters, polymethylmethacrylates, and copolymer/polymer blends. Rubber-modified polymers such as styrene elastomers, styrene/butadiene copolymers, ethylene elastomers, butadiene, and polybutylene resins, ethylene-propylene rubbers, EPDM, EPM, and other rubbery homopolymers and copolymers of such can be added to enhance softness and hand. Olefin elastomers can also be utilized for such purposes. Rubbers, including natural rubber, SBR, polybutadiene, ethylene propylene terpolymers, and vulcanized rubbers, including TPVs, can also be added to improve rubber-like elasticity.

Thermoplastic foam absorbency can be enhanced by foaming with spontaneous hydrogels, commonly known as superabsorbents. Superabsorbents can include alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, carboxy-methylcellulose, isobutylene maleic anhydride copolymers, and mixtures thereof. Further suitable polymers include inorganic polymers, such as polyphosphazene, and the like. Furthermore, thermoplastic foam biodegradability and absorbency can be enhanced by foaming with cellulose-based and starch-based components such as wood and/or vegetable fibrous pulp/flour.

In addition to any of these polymers, the foam polymer formula may also, or alternatively, include diblock, triblock, tetrablock, or other multi-block thermoplastic elastomeric and/or flexible copolymers such as polyolefin-based thermoplastic elastomers including random block copolymers including ethylene α-olefin copolymers; block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Polymers of Belpre, Ohio, U.S.A., under the trade designation KRATON® elastomeric resin or from Dexco, a division of ExxonMobil Chemical Company in Houston, Tex., U.S.A., under the trade designation VECTOR® (SIS and SBS polymers) or SEBS polymers as the SEPTON® series of thermoplastic rubbers from Kuraray America, Inc. in New York, N.Y., U.S.A.; blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E. I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide; thermoplastic elastic polyesters, including those available from E. I. Du Pont de Nemours Company, under the trade name HYTREL®, and ARNITEL® from DSM Engineering Plastics of Evansville, Ind., U.S.A., and single-site or metallocene-catalyzed polyolefins having a density of less than about 0.89 grams/cubic centimeter such as metallocene polyethylene resins, available from Dow Chemical Company in Midland, Mich., U.S.A. under the trade name AFFINITY™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are the rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight and having the same ratio of A blocks to B blocks. Diblocks with a different ratio of A to B blocks or a molecular weight larger or greater than one-half of triblock copolymers may be suitable for improving the foam polymer formula for producing low-density, soft, flexible, absorbent foam via polymer extrusion.

As illustrated in Examples 4 and 5 below, it may be particularly beneficial to include a thermoplastic elastomer having a high diblock content and high molecular weight as part of the foam polymer formula to extrude low-density, soft, flexible, resilient, absorbent, thermoplastic foam. For example, the thermoplastic elastomer may have a diblock content between about 50% and about 80%, by weight, of the total thermoplastic elastomer weight.

KRATON® products have been shown to act as a discontinuous phase in styrenic-based foams and act as cell-opener generators when used in small amounts. The amount of KRATON® polymers used in the foam polymer formula as a whole in the foam of the invention is of such a large magnitude that the cell-opener effect is negligible compared to the resiliency, flexibility, elasticity, and softness imparted.

Suitably, the foam polymer formula includes up to about 95%, by weight, of polystyrene, and at least 5%, by weight, of thermoplastic elastomer. More particularly, the foam polymer formula may include between about 50% and about 95%, by weight, of polystyrene, and between about 5% and about 50%, by weight, of thermoplastic elastomer. Alternatively, the foam polymer formula may include between about 50% and about 80%, by weight, of polystyrene, and between about 20% and about 50%, by weight, of thermoplastic elastomer. In one embodiment, for example, the foam polymer formula may include equal amounts of polystyrene and thermoplastic elastomer.

In accordance with the invention, a plasticizing agent can be included in the foam polymer formula. A plasticizing agent is a chemical agent that imparts flexibility, stretchability and workability. The type of plasticizing agent has an influence on foam gel properties, blowing agent migration resistance, cellular structure, including the fine cell size, and number of open cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer matrix upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the foam polymer formula. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In order for the foam to be used in personal care and medical product applications and many absorbent wiping articles and non-personal care articles, the foam must meet stringent chemical and safety guidelines. A number of plasticizing agents are FDA-approved for use in packaging materials. These plasticizing agents include: acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; and 3-(2-xenoyl)-1,2-epoxypropane.

In certain embodiments, the same material used as the thermoplastic elastomer may also be used as the plasticizing agent. For example, the KRATON® multi-phase polymers, described above, may be used as a thermoplastic elastomer and/or a plasticizing agent. In which case, the foam polymer formula may include between about 10% and about 50%, by weight, of a single composition that acts as both a thermoplastic elastomer and a plasticizing agent. Described in an alternative manner, the foam may be formed without a plasticizing agent per se; in which case, the foam polymer formula may include between about 10% and about 50%, by weight, of the thermoplastic elastomer. An example of such a composition is Sample 2a in Example 1, below.

Foaming of soft, flexible polymers, such as thermoplastic elastomers, to a low density is difficult to achieve. The addition of a plasticizing agent makes foaming to low densities even more difficult to achieve. The method of the invention overcomes this difficulty through the inclusion of a surfactant in the foam polymer formula. The surfactant stabilizes the cells, thereby counteracting cellular collapse while retaining an open-cell structure. This stabilization of the cells creates cell uniformity and control of cell structure. In addition to enabling foaming of plasticized thermoplastic elastomer polymer containing foam formulations to low densities, the surfactant also provides wettability to enable the resulting foam to absorb fluid.

While it is not intended to limit the invention to a particular theory, it is believed that improved cell stabilization is achieved via the use of surfactant in a foam polymer formula containing a plasticizing agent. The addition of a plasticizing agent makes foaming to low densities even more difficult to achieve. Plasticizing agents such as waxes, oils, silicon defoamers, and small particulates at low addition provide localized surface tension reduction in the foam cell membrane, which causes rupturing and premature cellular collapse or coalescence. The method of the invention overcomes this difficulty through the addition of surfactant to the foam polymer formula which counteracts thermodynamic and kinetic instabilities of bubble formation in the polymer melt. The surfactant stabilizes the cells, thereby counteracting cellular collapse caused by the plasticizing agent. This stabilization of the cells creates cell uniformity in terms of cell size and cell size distribution and thereby allows control of cell structure. Since the surfactant is a surface active agent, it lowers the surface or interfacial tension and thus assists bubble formation. A decreased surface tension reduces the pressure differential required to maintain a bubble of a certain size, reduces the pressure difference between bubbles of different sizes, reduces the free energy required to maintain a given interfacial area, and thus increases the bubble nucleation rate. As Gibbs theorem explains, a surfactant combats excessive thinning of cell membranes and restores surfactant concentration to the surface and thereby acts as a stabilizing factor; however, a surfactant does not restore liquid to the film, which results in a lack of self-repair. The Marangoni effect describes surface flow of dragging underlying layers of liquid to restore film thickness, which enhances film elasticity and resilience and thus counters cellular coalescence. This again is a stabilizer. Assuming the credence of these two mechanisms, a surfactant would be most effective if it is designed so that the Marangoni effect dominates the foam polymer formula, for if the Gibbs effect dominates, the diffusion rate would be too high and self-repair would not occur. Therefore the addition of surfactant acts as a "buffer" or "stabilizer" to control surface tension and with control of temperature, which also affects surface tension, melt viscosity and melt strength, bubble stability can occur so that cells form in the thermoplastic melt. This effect is offset by lowering the surface tension forces that hold the polymer matrix together.

Bubble walls typically drain due to gravity and capillary forces. Such drainage thins the walls before the cell struts are sufficiently hardened, which leads to cell collapse. La Place and Young proposed that capillary pressure at the junction of two or more ribs is lower, thereby creating flow from the membrane to the ribs and, consequently, thinning. With a sufficient amount of surfactant molecules arranged preferentially to migrate to the surface of the film membrane, the presence of surfactant at the membrane's thin film surfaces provides resistance to drainage of the molten plastic. If the film layer is sufficiently thick, such as in a foam membrane, it can be further stabilized by an ionic double layer of molecules resulting from orientation of ionic surfactants. Both nonionic and ionic surfactants can exhibit another stabilizing force if the membrane is sufficiently thin. This would be done by the alignment of surfactant tails to create a bi-layer structure, such as found in biological cells, that is held together via Van der Waals forces and thus stabilizes the foam membrane.

(References: *Polymeric Foams*, edited by Daniel Klempner and Kurt Frisch, Hanser Publishers, 1991; and *Foam Extrusion*, edited by S. T. Lee, Technomic Publishing Co., Inc., 2000.)

The surfactant is thought to also provide resistance to diffusion of the gas from the cell to the surroundings, which also aids in resisting collapse. The reduced gas permeability due to the drainage resistance is related to the degree the surfactant can pack into the bubble's film surface and explains the difference between the performances of the various surfactants. This reduced rate of diffusion allows sufficient cooling for strut formation to prevent coalescence. The surfactant does not need to prevent drainage, but simply slows it sufficiently so that the cell struts are substantially hardened thereby preventing cell coalescence. In general terms, it is expected that surfactants that are highly mobile in the melt, highly surface active, and can pack tightly and prevent membrane drainage will provide the best cell stabilization.

The surfactant may be a single surfactant, or a multi-component surfactant system. A multi-component surfactant system is a combination of two or more surfactants. It has been found that certain multi-component surfactant systems can achieve equal or better foam formation at a lower dosage than certain single-component surfactant systems. Example 3, below, illustrates the effects of adding various dosages of surfactant and surfactant mixtures to a polymer blend. For example, in the samples tested, the two-component surfactant foams had densities comparable to foam made with over three times the amount of a single-surfactant system. Surfactant is a costly component in the foam polymer formula. The use of certain multi-component surfactant systems can be used to achieve foam having comparable foam properties at a lower cost than foam that includes three times as much surfactant.

The surfactant can be included in the foam polymer formula in an amount between about 0.05% and about 10%, or between about 0.1% and about 5%, by weight, of the foam polymer formula. In an embodiment in which the surfactant is a multi-component surfactant system, the total of all surfactants can be included in the foam polymer formula in an amount between about 0.05% and about 8.0%, or between about 0.1% and about 3.0%, by weight, of the foam polymer formula. Examples of suitable surfactants include cationic, anionic, amphoteric, and nonionic surfactants. Anionic surfactants include the alkylsulfonates. Examples of commercially available surfactants include HOSTASTAT® HS-1, available from Clariant Corporation in Winchester, Va., U.S.A.; Cognis EMEREST® 2650, Cognis EMEREST® 2648, and Cognis EMEREST® 3712, each available from Cognis Corporation in Cincinnati, Ohio, U.S.A.; and Dow Corning 193, available from Dow Chemical Company in Midland, Mich., U.S.A. Alkyl sulfonates are quite effective; however, use of this class of surfactants in certain applications may be limited because of product safety. Some combinations offer unexpected benefits where the alkyl sulfonate is added at a substantially lower level in conjunction with another surfactant to yield good foaming and wettability. In one embodiment, for example, the surfactant can be added to the foam polymer formula in a gaseous phase, such as through the use of a blowing agent such as supercritical carbon dioxide. One benefit of using a gaseous surfactant is that the surfactant can fully penetrate and be incorporated into the polymer matrix, which can improve substantivity and thereby reduce surfactant fugitivity to enhance the foam's permanent wettability.

The balance between cell stabilization of the surfactant and the enhanced melt drainage from the plasticizing agent enables control over the open-cell content of the resulting foam. More particularly, the amount of surfactant can be adjusted to counteract the effects of the plasticizing agent, and/or the amount of the plasticizing agent can be adjusted to counteract the effects of the surfactant. For example, if the plasticizing agent is included in the foam polymer formula in an amount between about 0.5% and about 5%, by weight, of the foam polymer formula, then the surfactant should be included in the foam polymer formula in an amount between about 0.5% and about 5%, by weight, of the foam polymer formula. Similarly, if the plasticizing agent is included in the foam polymer formula in an amount between about 5% and about 10%, by weight, of the foam polymer formula, then the surfactant should be included in the foam polymer formula in an amount between about 2% and about 10%, by weight, of the foam polymer formula. In addition, the polymer resin melt flow index can be adjusted to offset the plasticizing agent's effect.

Other additives can be included in the foam polymer formula to enhance the properties of the resulting foam. For example, a nucleant can be added to improve foam gas bubble formation in the foam polymer formula. Examples of suitable nucleants include talc, magnesium carbonate, nanoclay, silica, calcium carbonate, modified nucleant complexes, and combinations thereof. An example of a commercially available nucleant is a nanoclay available under the trade name CLOISITE® 20A, from Southern Clay Products, Inc. in Gonzales, Tex., U.S.A. The nucleant can be added to the foam polymer formula in an amount between about 0.1% and about 5%, by weight, of the foam polymer formula. Nucleants, or nucleating agents, are described in greater detail below.

A blowing agent, described in greater detail below, can be added to the foam polymer formula to aid in the foaming process. Blowing agents can be compounds that decompose at extrusion temperatures to release large volumes of gas, volatile liquids such as refrigerants and hydrocarbons, or ambient gases such as nitrogen and carbon dioxide, or water, or combinations thereof. A blowing agent can be added to the foam polymer formula in an amount between about 1% and about 10%, by weight, of the foam polymer formula.

Once the foam polymer formula is mixed and formed, including the plasticizing agent, the surfactant, and any other additives, the foam polymer formula is heated and mixed, suitably to a temperature between about 100 and about 500 degrees Celsius, to create a polymer melt. The plasticizing agent reduces elongational viscosity of the polymer melt, which leads to foaming difficulties. However, the surfactant mediates the impact of the plasticizing agent on the viscosity, thereby providing control over the open-cell content of the resulting foam. Also, as mentioned, the polymer resin melt index can be adjusted to offset the plasticizing agent's effect.

The polymer melt can be foamed using any suitable foaming technique known to those skilled in the art. The density of the foam is suitably about 0.1 g/cm$^3$ or less, or about 0.05 g/cm$^3$ or less, or about 0.01 g/cm$^3$ or less. Foam expansion ratio is generally about 10 or greater. Suitably, the absorbent foam has about 5% or more closed cells, or about 10% or more closed cells, or about 15% or more closed cells to improve resiliency and/or compression resistance.

The polymer melt can be continuously extruded to form a soft, flexible, open-cell, thermoplastic, absorbent foam. As explained above, the open-cell content of the foam is controlled by adjusting the amounts of plasticizing agent and surfactant. Open-cell content can be measured using a gas pycnometer according to ASTM D2856, Method C. The open-cell content of the resulting foam is suitably about 50% or greater, or about 70% or greater, or about 80% or greater.

To produce thermoplastic foam for disposable personal care products, continuous plastic extrusion processes are typically utilized. (Certain injection molding and batch processes can also be employed.) Often tandem screw-type extruders are used because of the need for tight control of extrusion temperatures to produce open-cell foam. The first extruder typically contains several zones including: feed and conveying, compression, melting, metering and mixing zones and if one extruder is being used, a cooling zone is utilized prior to polymer melt discharge, foaming, and shaping. The first extruder is typically hopper loaded with resin and additives using dry/blend/metering equipment and/or having the additive(s) incorporated into the pelletized polymer concentrate such as in a masterbatch. The resins, additives, and/or masterbatch are then heated in the extruder to form a plasticized or melt polymer system, often with zoned temperature control using extruder cooling/heating systems. Physical blowing agents are typically added after the melt temperature has been heated to a temperature at or above its glass transition temperature or melting temperature to form a foamable melt. The inlet for a physical blowing agent is typically between the metering and mixing zones. The blowing agent is mixed thoroughly with the melted polymer at a sufficiently elevated pressure to prevent melt expansion. With a nucleating agent and blowing agent blended in the polymer melt, the foamable melt is typically cooled to a lower temperature to control the desired foam cell structure. With tandem extruders, the cooling is done in a second extruder which is connected downstream of the first extruder through a heated cross-over supply pipe. In single extruders, cooling is typically done upstream of the discharge orifice. Often cooling/heating systems with process temperature control loops are incorporated to tightly control foam bubble nucleation/growth within the melt. The optimum cooling temperature is typically at or slightly above the glass transition temperature or melting point of the melt. The melt is then extruded through a die to a lower pressure (typically atmospheric or a vacuum) to cause thermodynamic instability and foaming which then cools and crystallizes the plastic to form foam and solidifies to form a web or product. Often circular, annular or slit dies, including curtain dies, and the like are used, often with a mandrel, to shape and draw the web to the desired gauge, shape and orientation with foam expansion and cooling.

Various equipment configurations using such extrusion can be used to manufacture thermoplastic expanded foam, extruded sheet, stranded foam, rod, pipe, block, plank, film, and beads. Foam laminates and composites can also be made with such equipment. Various specialized equipment can be employed upstream of specially designed dies to enhance mixing, cooling, cellular structure, metering, and foaming and include static mixers, gear pumps, and various extruder screw designs. Stretching equipment, including roller nips, tenters, and belts, is sometimes used immediately downstream of discharge to elongate cellular shape to enhance absorbency. Microwave irradiation for cross-linking, foaming activation, and use of mechanical means can also be used to enhance foam properties. Foam contouring, shaping (e.g. use of a wire mesh pattern) and the like, using thermoforming, and other such thermal processes can be used to control shaping and absorbent swelling.

Both physical and chemical blowing agents, including both inorganic and organic physical blowing agents, are used to create foaming. Suitable inorganic physical blowing agents include water, nitrogen, carbon dioxide, air, argon, and helium. Organic blowing agents include hydrocarbons such as methane, ethane, propane, butanes, pentanes, hexanes, and the like. Aliphatic alcohols and halogenated hydrocarbons, including FREON® and HFC-134A, can also be used though in the latter, their use is generally avoided for environmental reasons. Endothermic and exothermic chemical blowing agents which are typically added at the extruder hopper include: azodicarbonamide, paratoluene sulfonyl hydrazide, azodiisobutyro-nitrile, benzene sulfonyl hydrazide, P-toluene sulfonyl hydrazide, barium azodicarboxylate, sodium bicarbonate, sodium carbonate, ammonium carbonate, citric acid, toluene solfonyl semicarbazide, dinitroso-pentamethylene-tetramine, phenyltetrazole sodium borohydride, and the like. Mixtures and combinations of various physical and chemical blowing agents can be used and often are used to control cell structure. Blowing agent activators can be added to lower the decomposition temperature/profile of such chemical blowing agents. Such activators include metals in the form of salts, oxides, or organometallic complexes.

Open-cell formation can be regulated by elevated processing pressures and/or temperatures and use of nucleating agents and chemical blowing agents which can control both cell density and cell structure. Various base resins are sometimes used to broaden the foaming temperature to make open-cell foam. Open-cell level can be facilitated by adding small amounts of various immiscible polymers to the foam polymer formula such as adding polyethylene or ethylene/vinyl acetate copolymer to polystyrenic-based foam systems to create interphase domains that cause cell wall rupture. By regulating the polymer system components and crystallization initiating temperature, open-cell content and microporous cell membrane uniformity can be controlled. Ethylene-styrene interpolymers can be added to alkenyl aromatic polymers to control open-cell quality and improve surface quality and processability. Small amounts of polystyrene-based polymers are sometimes added to polyolefin-based foams to increase open-cell content.

Additives, such as nucleating agents, can also be employed to obtain desired fine open-cell structure. The amount of nucleating agent will vary according to the cell structure desired, foaming temperature, pressure, polymer composition, and type of nucleating agent utilized. Typically with increasing nucleating agent, cell density and open-cell content increase. Nucleating agents include calcium carbonate, blends of citric acid and sodium bicarbonate, coated citric acid/sodium bicarbonate particles, nanoclays, silica, barium stearate, diatomaceous earth, titanium dioxide, talc, pulverized wood, clay, and calcium stearate. Stearic acid, salicylic acid, fatty acids, and metal oxides can also be used as foaming aids. Other thermoplastic polymers can also be used for such purposes. These are typically dry blended or added with the polymer concentrate.

Various additives such as lubricants, acid scavengers, stabilizers, colorants, adhesive promoters, fillers, smart-chemicals, foam regulators, various UV/infrared radiation stabilizing agents, antioxidants, flame retardants, smoke suppressants, anti-shrinking agents, thermal stabilizers, rubbers (including thermosets), anti-statics, permeability modifiers, and other processing and extrusion aids including mold release agents, and anti-blocking agents, and the like can also be added to the foam polymer formula.

Secondary post-treatment processes can be performed to further improve absorbency, fit, and similar properties including mechanical needling, stretching, brushing, scarfing, buffing/sanding, and drawing for controlling cellular orientation, aesthetics, and softening. Calendaring and creping can also be used to soften and rupture cell membranes to improve cellular connectivity, and thermoforming can be used to shape the foam absorbent. Often a foam surface skin may form during extrusion, which can later be skived or sliced off, needle-punched, brushed, scraped, buffed, scarved, sanded, or perforated to remove the barrier. Mechanical, hydraulic, thermal, or laser perforation can also be used to soften foam and further increase open-cell content.

Post-densification of the foam structure, after extrusion, can be employed to enhance functionality. The foam of the invention can be laminated to other layers, resulting in structures having various functionalities.

EXAMPLES

Example 1

Foam polymer formulas were made from blends of Dow STYRON® 685D polystyrene pelletized resin and KRATON® G1657 styrene-ethylene-butylene-styrene (SEBS) block copolymer pelletized thermoplastic elastomer resin. Low molecular weight polyethylene wax (Eastman EPOLENE® C-10) was added to certain samples to plasticize the foam polymer formula. A surfactant, Dow-Corning 193, available from Dow-Corning Company in Midland, Mich., U.S.A., was added to certain samples to improve wettability. A nucleating agent, CLOISITE® 20A, was also added at 5%, by weight, to the foam polymer formula. All foams were extruded using a 27-mm Leistritz co-rotating twin screw extruder, available from American Leistritz Extruder Corporation in Somerville, N.J., U.S.A., equipped for direct injection of carbon dioxide gas. The foam polymer formulas were heated to about 200 degrees Celsius in the extruder and subsequently foamed using carbon dioxide (added at 6%, by weight, of the foam polymer formula) as a blowing agent. Extrusion temperatures and pressures were adjusted for optimum foam expansion and open-cell connectivity. Table 1 shows the foam polymer formula for each of the six samples formed. Amounts are recorded in terms of percentage by weight of the foam polymer formula, with the foam polymer formula including: polystyrene, SEBS, nucleating agent, and, when present, surfactant/polyethylene wax.

TABLE 1

Foam Polymer Formulas

| Sample | Polystyrene | SEBS | PE Wax | Surfactant |
|---|---|---|---|---|
| 1a | 47.5% | 47.5% | 0% | 0% |
| 2a | 47.5% | 42.7% | 0% | 4.8% |
| 3a | 47.5% | 38.4% | 4.3% | 4.8% |
| 4a | 47.5% | 25.6% | 17.1% | 4.8% |
| 5a | 79.3% | 8.5% | 5.6% | 1.6% |
| 6a | 47.5% | 37.1% | 5.6% | 4.8% |

Each of the samples was tested to determine foam density, apparent open-cell content, compression modulus, resiliency, and strain. Table 2 shows a comparison of these foam properties for each of the samples. Also included in Table 2 for comparison purposes is RYNEL® 562-B, a commercially available absorbent foam from Rynel Ltd. Co. in Boothbay, Me., U.S.A. More particularly, 562-B is a medical-grade hydrophilic polyurethane foam. Though expensive for many disposable product applications and not readily process recyclable, such thermoset foam has been demonstrated to have functional absorbency, mechanical and aesthetic properties for personal care and medical foam applications.

Foam density was calculated using the basis weight measurement as described in ASTM D1622-98, and the bulk was measured using a hand micrometer and surface compression was avoided. Open-cell content was measured by a gas pycnometer using ASTM D2856, Method C. Compression modulus, resiliency, and strain were each measured using ASTM D3575. Modifications were made to the ASTM methods to accommodate sample geometries. The modifications were not made to change the outcome of the test. More particularly, the foam modulus and strain at 1 psi of pressure were measured in compression with a constant compression speed of 3 cm/min. The foam resiliency was determined by compressing a one-inch long sample, placed so that it had a height-to-length or -width aspect ratio of greater than 2.5, at a rate of 3 cm/min until a force of 5000 grams was reached. The sample was removed from the compressing force and the sample height was measured. The resiliency was determined by the final sample height divided by the original sample height (one inch).

TABLE 2

Foam Properties

| Sample | Foam Density (lb/ft³) | Open-Cell Content (%) | Modulus (psi) | Resiliency (%) | Strain (%) at 1 psi of pressure |
|---|---|---|---|---|---|
| 1a | 21 | 58 | 128 | — | 1.4 |
| 2a | 7 | 86 | 21 | 98 | 6.2 |
| 3a | 6 | 89 | 22 | 98 | 8.7 |
| 4a | 20 | 67 | 6 | — | 36.7 |
| 5a | 55 | 21 | — | — | — |
| 6a | 7 | 85 | 3 | 99 | 36.3 |
| RYNEL ® 562-B | 6 | 92 | 4.6 | 99–100 | 26.8 |

As shown in Table 2, the foam polymer formula without either a plasticizing agent or surfactant has a high density (Sample 1a). Sample 2a illustrates the substantial lowering of density through addition of surfactant alone. Sample 3a illustrates that density can be lowered even more and open-cell content can be raised through a combination of surfactant and plasticizing agent. Samples 4a and 5a illustrate the detrimental effect of an excessive amount of plasticizing agent with respect to the amount of surfactant.

Samples 5a and 6a, together, illustrate that foam expansion with higher levels of wax can be improved by increasing the level of the surfactant. With respect to Sample 5a, at a 1.6% surfactant loading, the foam density is 55 lb/ft³, which is nearly that of the raw unmodified polystyrene (65 lb/ft³), while with Sample 6a at a 4.8% surfactant loading (and with further addition of KRATON G1657, which is more difficult to foam than polystyrene), the foam density decreases to about 7 lb/ft³. Open-cell contents were measured at greater than 80% under such conditions.

Figure 2:
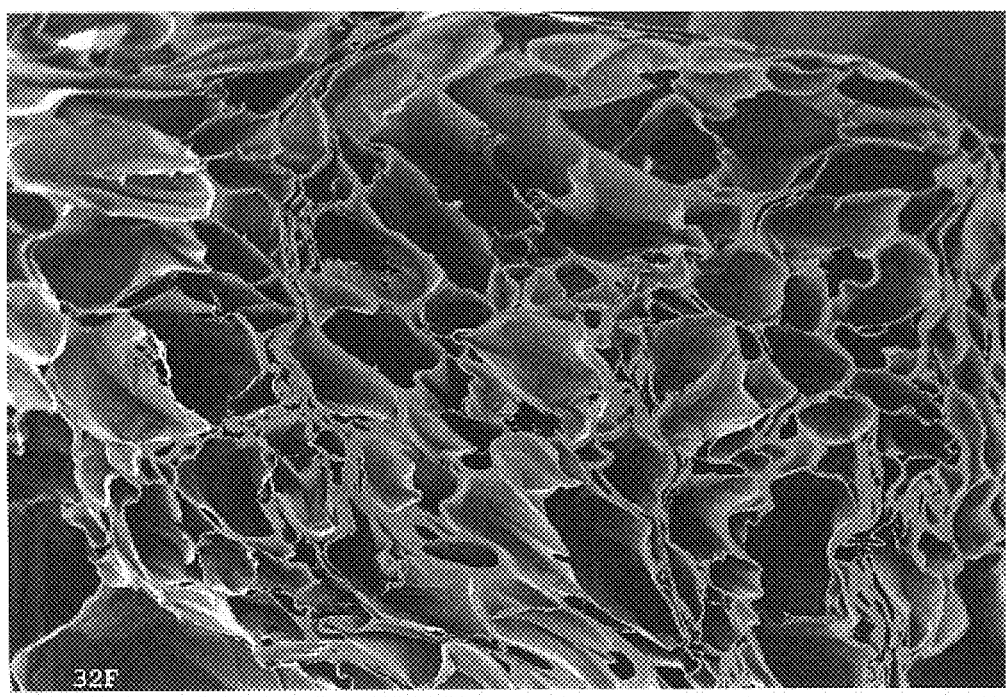
FIG. 2 is a photomicrograph of a cross-section of a foam, described in Example 1, taken by scanning electron microscopy. The photomicrograph was taken at a magnification of 15×.
Figure 3:
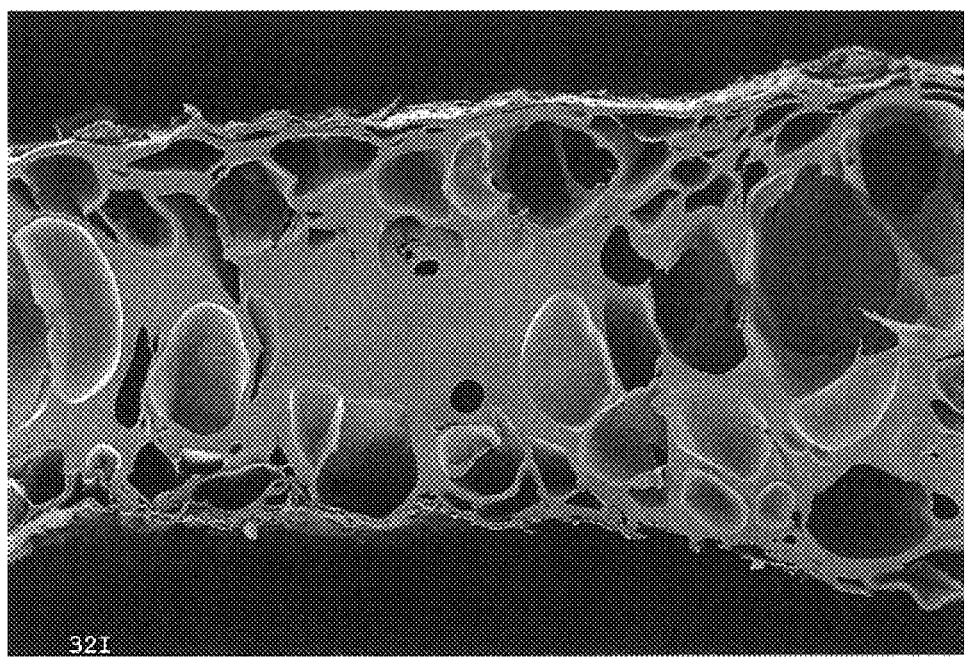
FIG. 3 is a photomicrograph of a cross-section of a foam, described in Example 1, taken by scanning electron microscopy. The photomicrograph was taken at a magnification of 15×.
Figure 4:
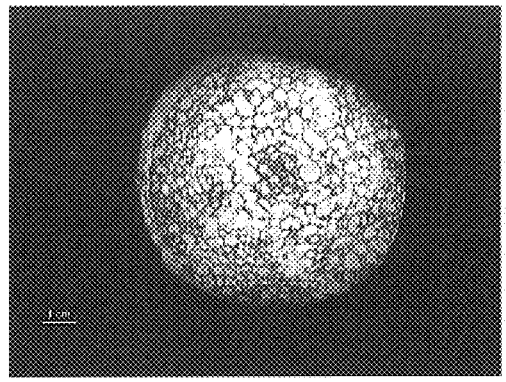
FIGS. 4–12 are photomicrographs of foam samples described in Example 3, taken by scanning electron microscopy. The photomicrographs were taken at a magnification of 20×.
Figure 5:
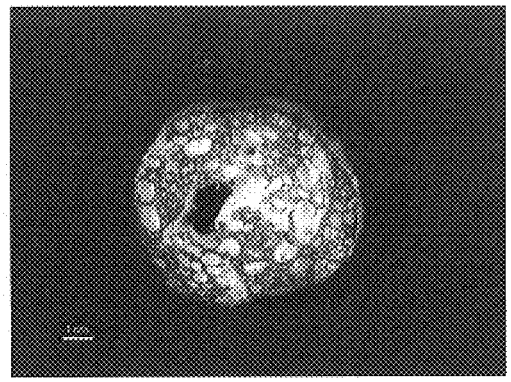
Figure 6:
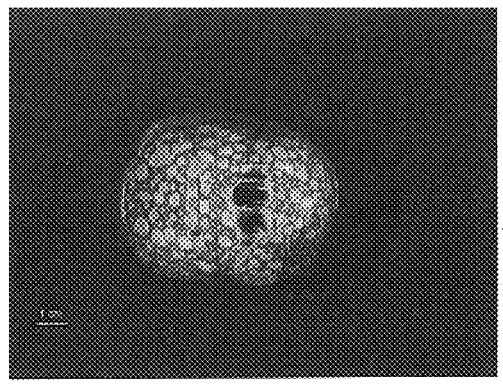
Figure 7:
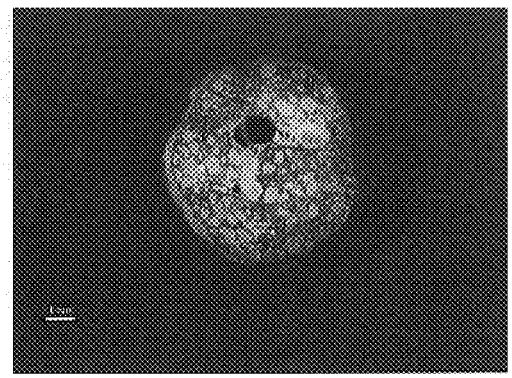
Figure 8:
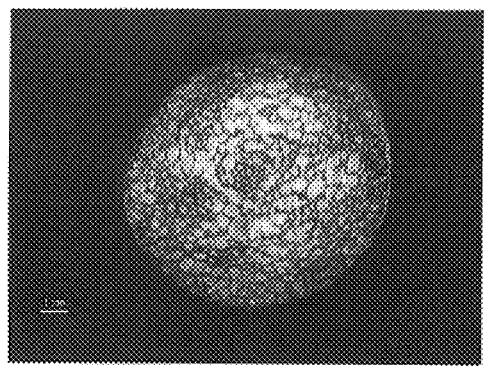
Figure 9:
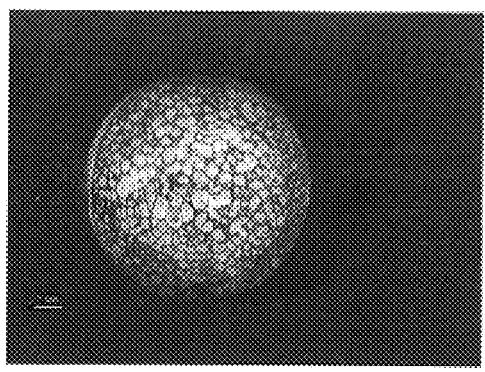
Figure 10:
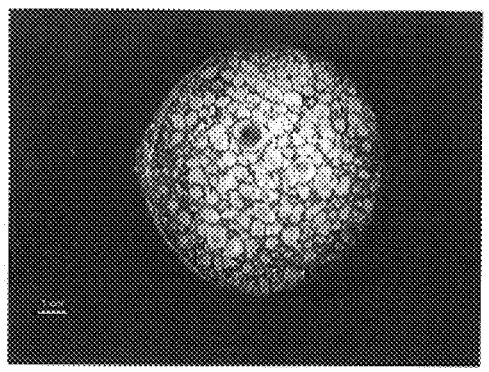
Figure 11:
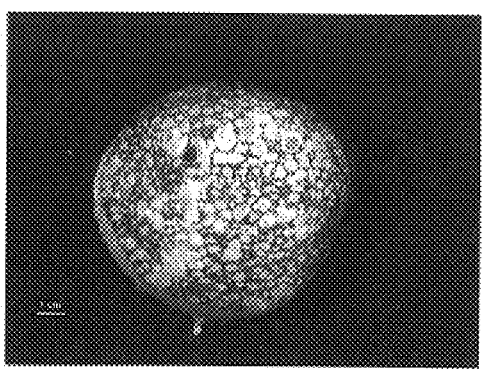
Figure 12:
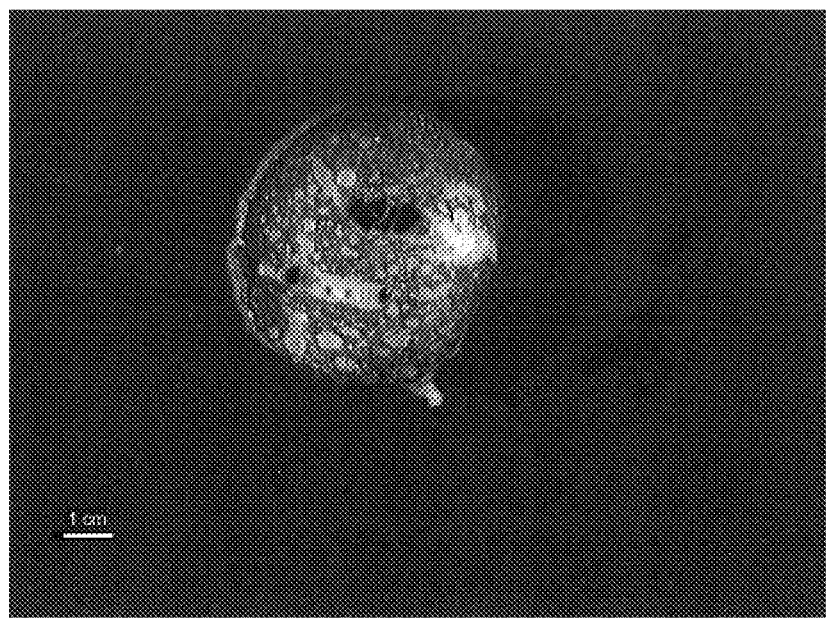
Figure 17:
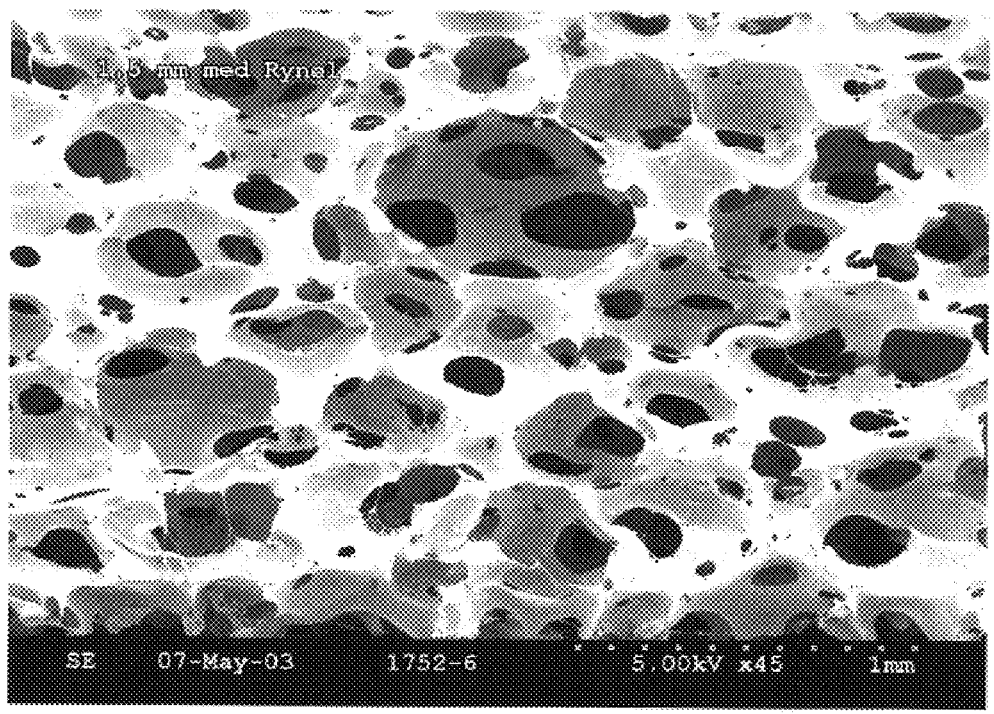
FIG. 17 is a photomicrograph of a cross-section of RYNEL® 562-B polyurethane absorbent medical-grade foam, taken by scanning electron microscopy. The photomicrograph was taken at a magnification of 45×.

Photomicrographs of Samples 2a, 3a, and 4a are provided in FIGS. 1–3, respectively. A photomicrograph of RYNEL® 562-B foam is shown in FIG. 17.

FIG. 1 shows the foam polymer formula without wax addition. The straight cellular walls indicate full cellular expansion with possible continued expansion while the foam polymer formula was cooling.

FIG. 2 shows the impact of adding 4.3% wax. The cell walls are corrugated. Gas was lost from the cells (possibly due to cell wall openings) and cells began to collapse after the cell walls were solidifying, but still soft. The result is the corrugated look of the cell walls.

FIG. 3 shows the impact of adding 17.1% wax. There are large areas that are not foamed. This is due to full collapse of the cells from too much plasticization.

Example 2

This example illustrates the importance of surfactant structure to enable the production of low-density foams from a blend of polystyrene with soft, flexible polymers. The foam polymer formula in this example included 50.0 parts of Dow STYRON 685D polystyrene and 45.2 parts of KRATON G1657 SEBS, and 4.8 parts CLOISITE 20A nanoclay. Foam extrusion method was the same as Example 1. Samples of the foam polymer formula with various surfactants, and levels of surfactant, and results of these samples are shown in Table 3.

TABLE 3

Foaming Soft, Flexible Polymers With Various Surfactants

| Sample | Surfactant Description | Surfactant Amount (parts per 100 parts of foam polymer formula) | Foam Density (lb/ft³) | Liquid Penetration into Foam | Open-Cell Content (%) |
|---|---|---|---|---|---|
| 1b | No Surfactant | 0 | 57 | No | 24 |
| 2b | Clariant HOSTASTAT HS-1 (sulfuric acid head C12–C18 saturated tail) | 2.7 | 7 | Yes | 84 |
| 3b | Dow Corning 193 (ethoxylated silicone polymer) | 4.6 | 13 | Yes | 76 |
| 4b | Cognis EMEREST 2650 (PEG 400 head C12 saturated tail) | 2.7 | 10 | No | 82 |
| 5b | Cognis EMEREST 2648 (PEG 400 head C18 unsaturated tail) | 2.7 | 13 | No | 57 |
| 6b | Cognis EMEREST 2712 (PEG 400 head C18 saturated tail) | 2.7 | 11 | No | 60 |

The results in Table 3 illustrate the impact of surfactant selection on foam density and wettability. Wettability is indicated by the penetration of five water droplets into the 5 mm thick foam through a de-skinned portion of the foam.

Sample 1b, the only sample without a surfactant, has a much higher density and a considerably lower open-cell content than each of the samples that includes a surfactant. There was no liquid penetration into the foam. Foams produced with HOSTASTAT HS-1 having a sulfuric acid head (Sample 2b) and Dow's ethoxylated silicon surfactant (Sample 3b) had liquid penetration while the Cognis surfactants with a PEG 400 head (Samples 4b–6b) had no liquid penetration, even with comparable open-cell content (Sample 4b vs. Samples 2b and 3b).

Example 3

This example illustrates the effect of multiple surfactants in comparison to single surfactants in the foam polymer formula. Table 4 illustrates the results of adding various dosages of surfactants and surfactant mixtures to a polymer blend of 54.45 parts of Dow STYRON 685D polystyrene, 44.55 parts of KRATON G1657 with 1 part of MISTRON® VAPOR talc, used as a nucleant, and available from Luzenac America, Inc., of Englewood, Colo., U.S.A. The surfactants utilized were: HOSTASTAT® HS-1, an alkyl sulfonate available from Clariant Corporation in Winchester, Va., U.S.A.; MMF 184 SW, an ethoxylated siloxane available from Siltech LLC in Dacula, Ga., U.S.A.; and MASIL® SF-19, an ethoxylated siloxane available from BASF Corporation in Mount Olive, N.J., U.S.A. Foam extrusion method was the same as Example 1 except that the maximum extrusion temperature utilized was 195 degrees Celsius and carbon dioxide addition rate was about 15%, by weight.

In Table 4, the foam saline intake rate is quantified by taking twelve sections of foam, each with a cleanly cut surface, and placing a drop of 0.9% NaCl saline solution on each surface. If the drop was absorbed rapidly enough that no meniscus was formed by the drop, that section was rated as 9. If the droplet was absorbed in one second or less but did form a meniscus, then the section was rated 5. If the droplet was absorbed between one second and ten seconds, the section was rated 3. If the droplet was not absorbed within ten seconds, then the section was rated 0. The average of the twelve sections tested is presented in Table 4.

TABLE 4

Comparison of Single-Surfactant and Multi-Surfactant Systems

| Sample | Surfactant | Dosage (surfactant parts per 100 parts of foam polymer formula) | Foam Density (lb/ft$^3$) | Foam Saline Intake Rating (0–9) |
| --- | --- | --- | --- | --- |
| 1c | HOSTASTAT HS-1 | 3 | 11 | 8.7 |
| 2c | HOSTASTAT HS-1 | 1 | 21 | 3.8 |
| 3c | MMF184SW | 3 | 18 | 3.3 |
| 4c | MMF184SW | 1 | 23 | 2.5 |
| 5c | MASIL SF-19 | 3 | 20 | 7.7 |
| 6c | MASIL SF-19 | 1 | 22 | 0.0 |
| 7c | 3 parts MASIL SF-19 + 1 part HOSTASTAT HS-1 | 1 | 12 | 5.7 |
| 8c | 4 parts MASIL SF-19 + 1 part HOSTASTAT HS-1 | 0.5 | 12 | 0.0 |
| 9c | 3 parts MMF184SW + 1 part HOSTASTAT HS-1 | 1 | 11 | 0.0 |
| 10c | 4 parts MMF184SW + 1 part HOSTASTAT HS-1 | 0.5 | 13 | 7.3 |
| 11c | None | 0 | 30 | 0.0 |

The results from Table 4 show that a mixture of the surfactants in the foam polymer formula at a dosage of 1 part surfactant per 100 parts of foam polymer formula produces foam with lower density than produced with 1 part surfactant per 100 parts of foam polymer formula of any of the single surfactants. Even at dosages of 0.5 parts of surfactant per 100 parts of foam polymer formula, the two-surfactant system showed synergy in producing lower density foam. The two-surfactant foams had densities comparable to foam made with over three times the amount of the best-performing single-surfactant system. The saline intake was somewhat reduced with the two-surfactant system; however, spontaneous fluid intake was still possible with low dosages of specific two-surfactant systems as measured by a saline intake rating of greater than 5 for Samples 7c and 10c.

Photomicrographs of some of the foam samples in Table 4 are presented in FIGS. 4–12. These figures further emphasize the synergy of the multi-surfactant system for foam extrusion. All photomicrographs are at a 20× magnification. The surface of the foam was stained red to aid in visual observation of the cell structure. These figures show the relative uniform cell structure provided by the multi-surfactant system.

Example 4

This example illustrates the effect of diblock copolymer content on the flexibility and absorbent properties of foams containing a thermoplastic elastomer (TPE).

Table 5 contains published information on the molecular properties of KRATON® thermoplastic elastomers used in this example. KRATON® thermoplastic elastomers are available from Kraton Polymers of Belpre, Ohio, U.S.A.

TABLE 5

Properties of KRATON® Thermoplastic Elastomers

| Polymer | Polystyrene Content (%) | Diblock Content (%) | Molecular Weight |
| --- | --- | --- | --- |
| KRATON® D1111 | 22% | 15% | |
| KRATON® D1119 | 22% | 66% | |
| KRATON® D1160 | 18.5% | | 168000–188000 |
| KRATON® D1161 | 15% | | 207000–237000 |

Various amounts of KRATON® D1111 and KRATON® D1119 were added to a blend of Dow STYRON® 685D polystyrene, Clariant HOSTASTAT® HS-1 antistatic agent, Ciba IRGAFOS® 168, a phosphate stabilizer that acts as a secondary antioxidant, available from Ciba Specialty Chemicals, Inc., Tarrytown, N.Y., U.S.A., and Luzenac MISTRON® Vapor Talc. These were added so that the composition was 62.5 parts of Dow STYRON® 685D, 33.6 parts of KRATON® polymer(s), 2.8 parts of Clariant HOSTASTAT® HS-1, 0.9 parts of Luzenac MISTRON® Vapor Talc and 0.2 parts of Ciba IRGAFOS®168. Table 6, from published Kraton literature, describes the amount of each KRATON® polymer added in each sample and the effective amount of diblock copolymer. Foam extrusion method was the same as Example 1 except that the maximum extrusion temperature utilized was 195 degrees Celsius and carbon dioxide addition rate was between 12% and 14%, by weight.

TABLE 6

Diblock Content of Samples Containing KRATON® Thermoplastic Elastomers

| Sample | KRATON® D1111 | KRATON® D1119 | Diblock Content (%) |
| --- | --- | --- | --- |
| 1d | 100 | 0 | 15% |
| 2d | 66 | 34 | 32% |
| 3d | 0 | 100 | 66% |

Foam Samples 1d–3d were extruded using a 27-mm Leistritz co-rotating twin screw extruder equipped for direct injection of carbon dioxide gas. The carbon dioxide was injected at a rate of 10–12 ml./min. and polymer was extruded at a rate of 4.5 lbs./hr. Extrusion temperatures and pressures were adjusted to obtain maximum foam expansion. Properties of the foam are presented in Table 7. The foam modulus and bending pressure were measured by compression of the foam sample between two plates. The foam sample, one inch in length by less than 0.4 inch in diameter, was placed with the long dimension positioned perpendicular to the compression plates. The plates were compressed at a constant rate of 5 cm/min. and the force to achieve this rate was recorded. The force was normalized using the cross-sectional area of the sample in contact with the compressing plates, yielding units of pressure. The pressure required to bend the sample, which appeared as the maximum pressure, was the bending pressure. The modulus was identified as the slope of the pressure in the limit of zero strain (approaching no compression of the sample).

Open-cell content was measured using a gas pycnometer utilizing ASTM D2856 method C. Foam saline fluid intake rating was measured by the following method: a specimen is cut to a 0.25 inch width (foam oriented MD) and placed so that a cut edge is perpendicular to gravity. One droplet of 0.9% NaCl saline solution is placed onto the specimen. If the droplet is immediately absorbed, the intake rating of 9 is given to the specimen. If the droplet is absorbed within a second but is slow enough that a meniscus is formed on the surface, the intake rating for the specimen is assigned a value of 5. If the droplet is absorbed within five seconds, the fluid intake rating of the specimen is 3. If a substantial amount of fluid is absorbed into the foam but the droplet is not completely absorbed within five seconds, the specimen intake rating is assigned a value of 1. The specimen intake rating is zero if little or none of the droplet is absorbed by the foam within five seconds. The reported rating is the average of at least twelve tested specimens. A fluid intake rating of 5 or greater is desirable for use in high-flow absorbent applications such as diapers.

TABLE 7

Properties of Foams Having Various Diblock Content

| Sample | Foam Density (lb/ft$^3$) | Foam Modulus (psi) | Bending Pressure (psi) | Open-Cell Content (%) | Foam fluid Saline Intake Rating (0–9) |
|---|---|---|---|---|---|
| 1d | 11 | 2880 | 166 | 69% | 8.7 |
| 2d | 9 | 740 | 132 | 69% | 7.0 |
| 3d | 6 | 259 | 30 | 69% | 9.0 |

As can be seen from Samples 1d, 2d, and 3d, increasing the amount of diblock copolymer in the thermoplastic elastomer reduces the foam density and decreases the foam stiffness as measured by modulus and bending pressure. The increase of diblock content in the thermoplastic elastomer did not impact the open-cell content and all samples had high fluid intake ratings.

Figure 18:
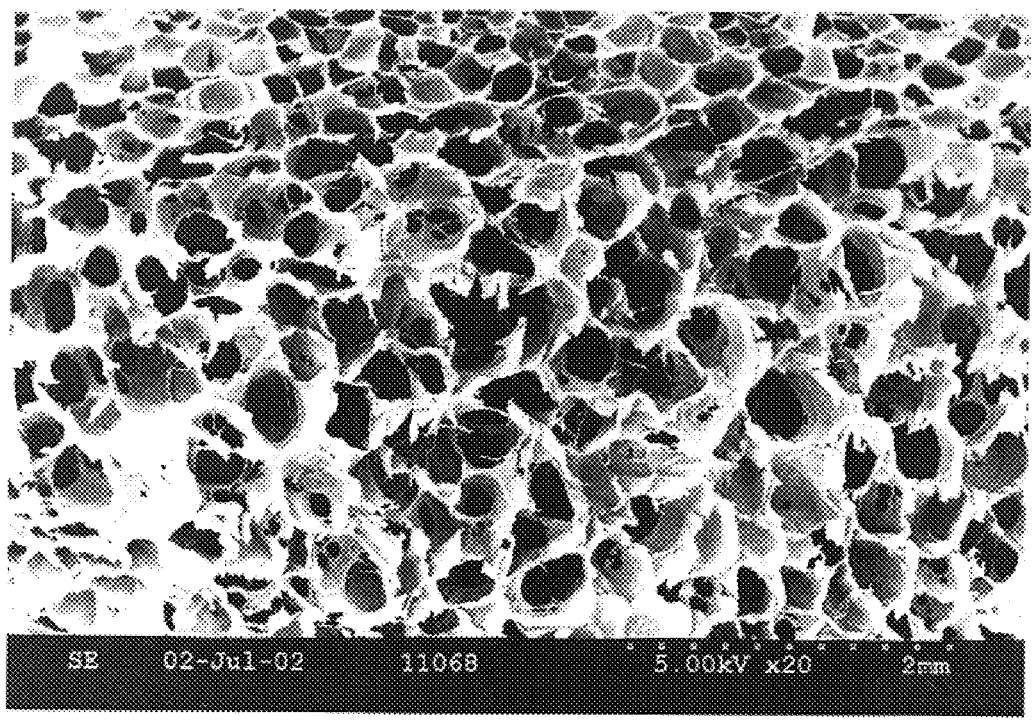
FIG. 18 is a photomicrograph of a cross-section of GEN-PAK® polystyrene absorbent meat tray foam, taken by scanning electron microscopy. The photomicrograph was taken at a magnification of 20×.

Table 8 displays the absorbent properties of foam Sample 3d of the invention compared to commercially available foams. RYNEL® 562-B is a soft, flexible, medical-grade hydrophilic polyurethane foam, available from Rynel Ltd. Co. in Boothbay, Me., U.S.A. Absorbent polystyrene-based open-cell rigid meat-tray foam from Genpak LCC: Food Service Division in Glens Falls, N.Y., U.S.A., is also provided for comparison. FIG. 18 is a photomicrograph of the GENPAK® foam. The absorbent properties displayed by the foam of the invention are similar to many of the absorbent properties of the commercially available Rynel foam. However, the foam of the invention is advantageous in that it is thermoplastic foam and is therefore recyclable, unlike thermoset foams such as Rynel foam. The GENPAK® polystyrene foam is not as absorbent and is not soft, flexible, and resilient as is the foam of the invention.

More particularly, the absorbent capacity of the tabled foam samples was tested using 0.9% NaCl solution in accordance with the Saturated Capacity Test Method, described herein. The viscous fluid capacity was tested according to the Saturation Capacity and Retention Capacity Test Method, described herein, using menses simulant. The Fluid Intake Flux of each foam sample was tested using 0.9% NaCl solution in accordance with the Fluid Intake Flux Test Method (Rynel and Genpak® foams) or Modified Fluid Intake Flux Test (Sample 3d), described herein. Additionally, the vertical capillarity of each foam sample was tested using 0.9% NaCl solution, in accordance with the Vertical Wicking Test Method, described herein.

TABLE 8

Absorbent Properties of Foams

| Sample | 0.9% NaCl Saturated Capacity (g/g) and Viscous Fluid Saturation Capacity/Retention Capacity (g/g) | | Fluid Intake Flux 0.9% NaCl 3 Insults (ml/sec/in$^2$) | | | Vertical Wicking in 30 mins. |
|---|---|---|---|---|---|---|
| | 0.9% NaCl | Menses Simulant | 1$^{st}$ Insult | 2$^{nd}$ Insult | 3$^{rd}$ Insult | (cm) 0.9% NaCl |
| 3d | 4.0 | 4.9/2.3 | 6.5 | 2.4 | 1.9 | 7.6 |
| RYNEL® 562-B | 9.0 | 16.4/3.5 | 2.7 | 2.0 | 1.9 | 7.0 |
| GENPAK® PS absorbent meat tray | 2.2 | | 0.2 | 0.1 | 0.1 | 3.9 |

Additionally, Samples 2b (Example 2) and 3d (Example 4) were tested for surfactant permanence in accordance with the Surfactant Permanence Test, described herein. It was found that Sample 2b had 0.00045 g of surfactant dissolved from a total possible of 0.0325 g, which is 1.39% dissolved and 98.61% remaining in the foam after a 24-hour soak. Sample 3d had 0.000288 g of surfactant dissolved from a total possible of 0.018 g, which is 1.6% dissolved and 98.4% remaining in the foam after a 24-hour soak.

Example 5

This example illustrates the effect of thermoplastic elastomer molecular weight on the flexibility and absorbent properties of foams.

KRATON® D1160 and KRATON® D1161 were each added to a blend of Dow STYRON®685D polystyrene, Clariant HOSTASTAT® HS-1 antistatic agent, Ciba IRGAFOS® 168 and Luzenac MISTRON® Vapor Talc. These were added so that the composition was 62.5 parts of Dow STYRON® 685D, 33.6 parts of KRATON® polymer, 2.8 parts of Clariant HOSTASTAT® HS-1, 0.9 parts of Luzenac MISTRON® Vapor Talc, and 0.2 parts of Ciba IRGAFOS® 168. This was done to discern the impact of thermoplastic elastomer molecular weight on foam properties, which are given in Table 9. The sample foams were extruded in a 27 mm Leistritz co-rotating twin screw extruder equipped for direct injection of carbon dioxide gas. The carbon dioxide was injected at a 6–12% loading, by weight, and polymer was extruded at a rate of 4.5 lb/hr. Extrusion temperatures and pressures were adjusted to obtain maximum foam expansion. The increased molecular weight of KRATON® D1161 (Sample 2e) compared to KRATON® D1160 (Sample 1e) provided for a foam of a lower density. The reduced modulus and bending pressure of Sample 2e compared to Sample 1e is due to the combination of the increased molecular weight and decreased polystyrene content of KRATON® D1161 compared to KRATON® D1160. In addition, it was qualitatively observed that with TPE included in the foam polymer formula in the foam samples, the foam was elastic and resilient in the X, Y and Z planar dimensions. This was seen by the stretch, recovery, and compression resiliency properties of the invention foams. Edge-wise compression is one means of measuring such resilient and elastic properties. The differences between these two thermoplastic elastomers also amounted to differences in the open-cell content and 0.9% NaCl saline Fluid Intake Rating.

TABLE 9

Foam Properties of Foams Having Different Molecular Weight TPE

| Sample | KRATON ® Polymer | Foam Density (lb/ft³) | Foam Modulus (psi) | Bending Pressure (psi) | Open-Cell Content (%) | Fluid Intake Rating (0–9) |
|---|---|---|---|---|---|---|
| 1e | D1160 | 20 | 8185 | >244 | 56% | 5.0 |
| 2e | D1161 | 16 | 887 | 62 | 64% | 8.0 |

Based on these results, it is desirable to utilize a thermoplastic elastomer with high diblock content and high molecular weight as part of the foam polymer formula to extrude low-density, soft, flexible, resilient, elastic, absorbent, thermoplastic foam.

Test Methods

Saturated Capacity Test Method

Saturated Capacity is determined using a Saturated Capacity (SAT CAP) tester with a Magnahelic vacuum gage and a latex dam, comparable to the following description. Referring to FIGS. 13–15, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are sufficiently thick to withstand the anticipated vacuum pressures, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex dam sheet 130 is looped around a dowel member 132 to facilitate grasping and to allow a convenient movement and positioning of the latex dam sheet 130. In the illustrated position, the dowel member 132 is shown supported in a hanger assembly 128 to position the latex dam sheet 130 in an open position away from the top of the vacuum chamber 112.

A bottom edge of the latex dam sheet 130 is clamped against a rear edge support member 134 with suitable securing means, such as toggle clamps 140. The toggle clamps 140 are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the vacuum apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 6 mm (0.25 inch) mesh TEFLON®-coated screening 148, available from Eagle Supply and Plastics, Inc., in Appleton, Wis., U.S.A., which measures 23.5 inches by 14 inches, is placed on top of the egg crating material 146.

A suitable drain line and a drain valve 150 connect to bottom plate member 119 of the vacuum chamber 112 to provide a convenient mechanism for draining liquids from the vacuum chamber 112. The various wall members and support members of vacuum apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0–100 inches of water, such as a No. 2100 gauge available from Dwyer Instrument Incorporated in Michigan City, Ind., U.S.A.

The dry product or other absorbent structure is weighed and then placed in excess 0.9% NaCl saline solution and allowed to soak for twenty minutes. After the twenty minute soak time, the absorbent structure is placed on the egg crate material and mesh TEFLON®-coated screening of the Saturated Capacity tester vacuum apparatus 110. The latex dam sheet 130 is placed over the absorbent structure(s) and the entire egg crate grid so that the latex dam sheet 130 creates a seal when a vacuum is drawn on the vacuum apparatus 110. A vacuum of 0.5 pounds per square inch (psi) is held in the Saturated Capacity tester vacuum apparatus 110 for five minutes. The vacuum creates a pressure on the absorbent structure(s), causing drainage of some liquid. After five minutes at 0.5 psi vacuum, the latex dam sheet 130 is rolled back and the absorbent structure(s) are weighed to generate a wet weight.

The overall capacity of each absorbent structure is determined by subtracting the dry weight of each absorbent from the wet weight of that absorbent, determined at this point in the procedure. The 0.5 psi SAT CAP or SAT CAP of the absorbent structure is determined by the following formula:

$$SAT\ CAP = (\text{wet weight} - \text{dry weight})/\text{dry weight};$$

wherein the SAT CAP value has units of grams of fluid/gram absorbent. For both overall capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example SCOTT® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

Fluid Intake Flux Test

Figure 16A:
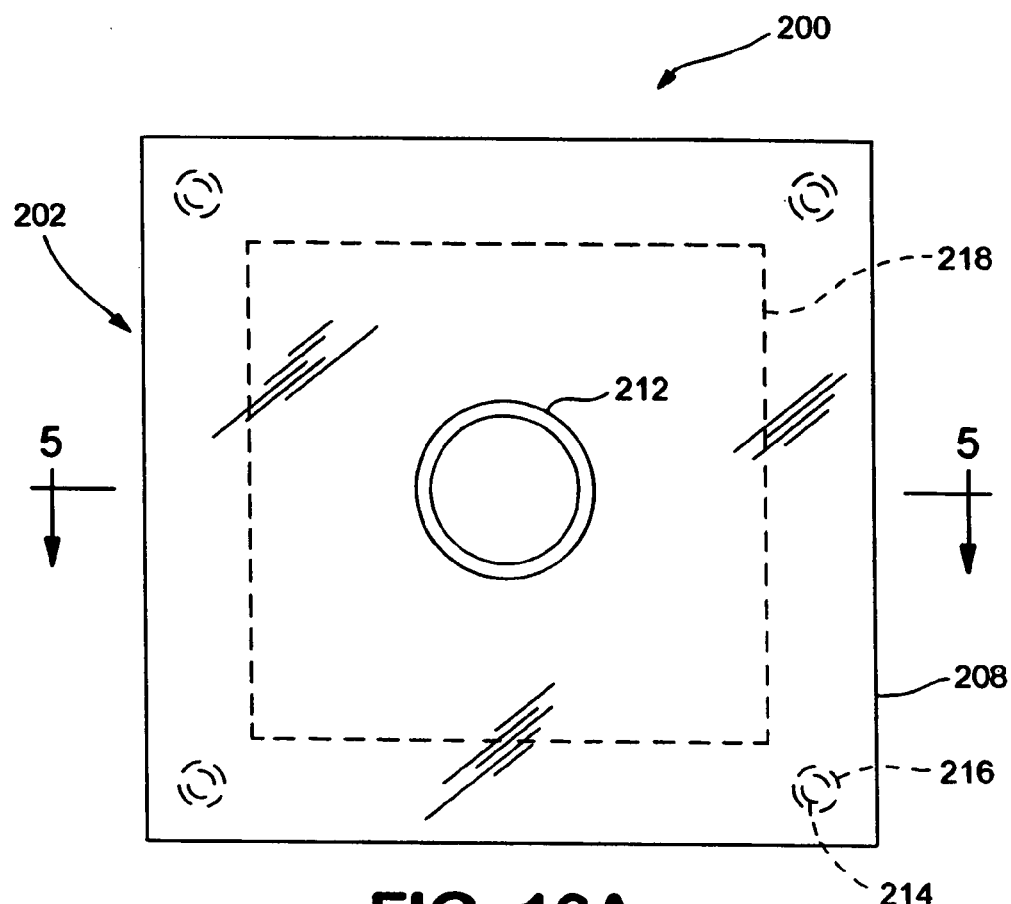
FIGS. 16A–16B representatively show a top view and a side view, respectively, of the test apparatus employed for the Fluid Intake Flux Test.
Figure 16B:
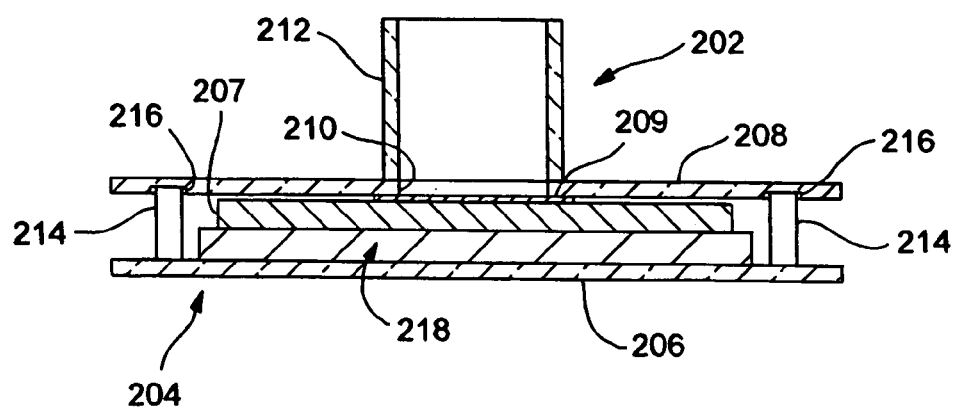

The Fluid Intake Flux (FIF) Test determines the amount of time required for an absorbent structure, and more particularly a foam sample thereof, to take in (but not necessarily absorb) a known amount of test solution (0.9 weight percent solution of sodium chloride in distilled water at room temperature). A suitable apparatus for performing the FIF Test is shown in FIGS. 16A and 16B and is generally indicated at 200. The test apparatus 200 comprises upper and lower assemblies, generally indicated at 202 and 204 respectively, wherein the lower assembly comprises a generally 7 inch by 7 inch square lower plate 206 constructed of a transparent material such as PLEXIGLAS® for supporting the absorbent foam sample during the test and a generally 4.5 inch by 4.5 inch square platform 218 centered on the lower plate 206.

The upper assembly 202 comprises a generally square upper plate 208 constructed similar to the lower plate 206 and having a central opening 210 formed therein. A cylinder (fluid delivery tube) 212 having an inner diameter of about one inch is secured to the upper plate 208 at the central opening 210 and extends upward substantially perpendicular to the upper plate. For flux determination, the inside dimension of the fluid delivery tube should maintain a ratio between 1:3 and 1:6 of the sample diameter. The central opening 210 of the upper plate 208 should have a diameter at least equal to the inner diameter of the cylinder 212 where the cylinder 212 is mounted on top of the upper plate 208. However, the diameter of the central opening 210 may instead be sized large enough to receive the outer diameter of the cylinder 212 within the opening so that the cylinder 212 is secured to the upper plate 208 within the central opening 210.

Pin elements 214 are located near the outside corners of the lower plate 206, and corresponding recesses 216 in the upper plate 208 are sized to receive the pin elements 214 to properly align and position the upper assembly 202 on the lower assembly 204 during testing. The weight of the upper assembly 202 (e.g., the upper plate 208 and cylinder 212) is approximately 360 grams to simulate approximately 0.11 pounds/square inch (psi) pressure on the absorbent foam sample during the FIF Test.

To run the FIF Test, an absorbent foam sample 207 being three inches in diameter is weighed and the weight is recorded in grams. The foam sample 207 is then centered on the platform 218 of the lower assembly 204. To prevent unwanted foam expansion into the central opening 210, centered on top of the foam sample 207, is positioned an approximately 1.5 inch diameter piece of flexible fiberglass standard 18×16 mesh window insect screening 209, available from Phifer Wire Products, Inc., Tuscaloosa, Ala. The upper assembly 202 is placed over the foam sample 207 in opposed relationship with the lower assembly 204, with the pin elements 214 of the lower plate 206 seated in the recesses 216 formed in the upper plate 208 and the cylinder 212 is generally centered over the foam sample 207. Prior to running the FIF test, the aforementioned Saturated Capacity Test is measured on the foam sample 207. Thirty-three percent (33%) of the saturation capacity is then calculated; e.g., if the test foam has a saturated capacity of 12 g of 0.9% NaCl saline test solution/g of test foam and the three inch diameter foam sample 207 weighs one gram, then 4 grams of 0.9% NaCl saline test solution (referred to herein as a first insult) is poured into the top of the cylinder 212 and allowed to flow down into the absorbent foam sample 207. A stopwatch is started when the first drop of solution contacts the foam sample 207 and is stopped when the liquid ring between the edge of the cylinder 212 and the foam sample 207 disappears. The reading on the stopwatch is recorded to two decimal places and represents the intake time (in seconds) required for the first insult to be taken into the absorbent foam sample 207.

A time period of fifteen minutes is allowed to elapse, after which a second insult equal to the first insult is poured into the top of the cylinder 212 and again the intake time is measured as described above. After fifteen minutes, the procedure is repeated for a third insult. An intake flux (in milliliters/second) for each of the three insults is determined by dividing the amount of solution (e.g., four grains) used for each insult by the intake time measured for the corresponding insult. The intake rate is converted into a fluid intake flux by dividing by the area of the fluid delivery tube, i.e., 0.79 in$^2$.

At least three samples of each absorbent test foam is subjected to the FIF Test and the results are averaged to determine the intake time and intake flux of the absorbent foam.

Modified Fluid Intake Flux (FIF) Test for Smaller Foam Samples

The test is done in a similar same manner as described in the aforementioned standard Fluid Intake Flux (FIF) test; however, this test was modified to accommodate smaller samples and yet keep the same fluid delivery tube to sample size ratio as in the standard FIF test. The modifications included installing the small sample of non-swelling foam that is to be tested into a suitable holder and using a suitable fluid delivery tube. The suitable holder can be an inverted laboratory glass funnel having a uniform diameter cylindrical output tube of one inch long that rests on top of an adjustable lab jack platform positioned for downward gravitational flow. The foam, of sufficient diameter (between 0.18 inch and 0.36 inch) and one inch in length, is gently positioned into the top of the uniform diameter glass tube of the inverted funnel that is sufficient in size to hold the foam without significant compression so that one end faces vertically up (proximal end) and the other end is facing downward (distal end). The glass tube holds the foam in a stationary position and is sufficient in length to hold the foam sample yet then immediately enlarges to the funnel opening to avoid discharging flow complications of excess fluid after the fluid leaves the foam's distal end. A fluid delivery tube is constructed with a 0.06 inch diameter orifice and a throat length that enlarges to a diameter enabling easy dispensation of fluid into the tube. The enlargement occurs at an approximately 0.25 inch length upstream of the orifice. The fluid delivery tube is positioned directly above the proximal end of the foam sample and the inverted funnel and the foam sample is raised using the lab jack such that the fluid delivery tube is brought into contact with the foam. Afterwards, similar to the standard FIF test, thirty-three percent (33%) of the saturation capacity for the foam sample is then calculated and this volume of 0.9% NaCl saline solution is dispensed using a PIPETMAN® P-200 µl pipette, available from Gilson, Inc. in Middleton, Wis., U.S.A., or similar pipette, into the fluid delivery tube which measures 0.06 inches in discharge orifice diameter, as opposed to a 1-inch diameter as described in the standard FIF Test, and the rate of flow is measured with a stopwatch as earlier described. The preference is to utilize the earlier described standard FIF test rather than the Modified FIF test and, if discrepancies exist, the standard FIF test is relied upon.

Vertical Wicking Test Method

A sample of foam is cut and mounted so that it hangs in a vertical orientation to gravity with an exposed foam edge in a substantially horizontal orientation. A sufficiently large reservoir of 0.9% NaCl saline test solution is raised, using a standard lab jack, so that the foam's horizontal edge extends approximately two millimeters beneath the surface of the saline. A timer is started simultaneous to the penetration of the foam into the saline. After thirty minutes, the height of the fluid in the foam is measured relative to the surface of the saline. If desired, the saline can contain a non-surface active, non-chromatographic dye to aid in identifying the penetration and wicking of the test fluid within the foam. Alternatively, the foam may be marked at the surface of the fluid and the fluid reservoir lowered to remove further contact with the foam. To compensate for possible foam expansion upon hydration, the foam may be marked at the fluid surface after the wicking time. Measurement of the fluid height in the foam using the initial foam dimensions may be done via appropriate means including x-ray imaging, optical measurement, or slicing sections of the foam until 0.9% NaCl saline test solution is apparent in the slice. For example in Sample 3d, the vertical wicking height was measured by optical methods and confirmed with x-ray imaging. Sample 3d did not expand; therefore, compensating for expansion was not necessary.

Surfactant Permanence Test

The Surfactant Permanence Test is based upon the surface tension depression effect by surfactant addition to water. The surface tension is measured by the duNoüy ring tensiometer method utilizing a Krüss Processor Tensiometer—K 12 instrument, available from Krüss USA in Charlotte, N.C., U.S.A. In general terms, a sample of foam is soaked in distilled water and the surface tension of the supernatant is measured. This surface tension is compared to a calibration curve to determine the amount of surfactant washed from the foam.

Test preparation includes creating a calibration curve for the particular surfactant utilized. This curve shows the reduced surface tension of the solution as surfactant concentration increases. At concentrations above the critical micelle concentration (CMC), the surface tension reduction from additional surfactant is minimal.

A sample of pre-weighed foam is placed in distilled water. The sample is immersed in the room temperature water for 24 hours, allowing fugitive surfactant to leach out of the foam and dissolve into the water. The amount of water used is critical. If the amount of surfactant leached into the water creates a concentration greater than the CMC, measurement of surface tension on the solution will only indicate that the concentration is greater than the CMC. The amount of distilled water used to wash the foam is 100 times the weight of the foam. After the 24-hour soak, the foam is removed from the water/surfactant solution (supernatant). The water in the foam is allowed to drain into the supernatant and gentle pressure is applied to the foam to aid in the removal of excess supernatant in the foam. The surface tension of the total supernatant is then measured. Utilizing the calibration curve, the surface tension corresponds to a weight fraction of surfactant in the water. This weight fraction is then multiplied by the total amount of water to yield the weight of surfactant leached from the foam. The amount of surfactant removed can be expressed as a fraction of the total surfactant in the initial foam. For example: foam is made with 10 parts surfactant for every 90 parts foam. A 100 gram sample is soaked in 10,000 grams of distilled water. The surface tension measurement of the supernatant indicates that the surfactant concentration in the supernatant is 0.03%. The amount of surfactant dissolved from the foam is 3.0 grams. The amount of surfactant in the initial foam was 10 grams, so 30% of the surfactant was dissolved and 70% of the surfactant remains in the foam.

With Clariant HOSTASTAT® HS-1, the CMC is at a concentration of 0.03%, by weight. At concentrations less than the CMC, the surface tension is described by: $\sigma = 5 \ln([s]) - 18$ where $\sigma$ is the surface tension and $[s]$ is the weight fraction of the surfactant. As an example, 2.96 grams of an open-cell polystyrene foam made with 2.5 parts HOSTASTAT® HS-1 to 100 parts polystyrene was immersed in 297.79 grams of distilled water for 24 hours. The surface tension of the supernatant was measured at 39 dynes/cm which corresponds to 0.0027 grams of surfactant dissolved into the water, or 3.7% of the total surfactant; therefore, 96.3% of the surfactant remained in the foam after a 24 hour wash.

Viscous Fluid Saturated Capacity and Retention Capacity Test

The saturation capacity and the retention capacity can be determined by soaking a 3.81 cm×3.81 cm×2 mm (a comparable 14.5 square centimeter surface area if smaller samples are tested, and if thicker samples are used, they will need to be sliced down using conventional non-densifying means) sample of absorbent foam in approximately 30 milliliters of a menses simulant test fluid (described below) in a plastic dish that is sufficient to fully saturate the sample for thirty minutes. The pre-weighed foam is placed on a strip of scrim-like material (for sample handling), then placed into the 30 milliliters of test fluid making sure fluid completely covers the sample. The dish is covered so evaporation does not occur. While soaking thirty minutes, the test fluid amount is monitored so that there is always excess fluid. The foam sample is then removed using the scrim and placed between two pieces of approximately 4-inch by 4-inch through-air-bonded-carded web material and on the outside of this sandwich; a layer of approximately 4-inch by 4-inch blotter paper is positioned on each side such that the blotter paper is facing the outside. A description of these materials is provided below. A pressure of 0.05 psi (0.345 KPa) is applied for five minutes to remove any pools of liquid. The saturated sample is then weighed. The weight of the liquid held in the foam sample divided by the dry weight of the foam sample is the saturation capacity of the sample.

After the saturated foam sample is weighed, the absorbent foam sample is placed in a centrifuge and spun at 300 G for three minutes so that the free fluid is discharged. The spun foam sample is then weighed. The weight of the liquid remaining in the spun foam sample divided by the dry weight of the sample is the retention capacity of the foam sample.

Accordingly:

a. Saturation Capacity=(Wet Wt. Before Centrifuge−Dry Wt.)/(Dry Wt.)

b. Retention Capacity=(Wet Wt. After Centrifuge−Dry Wt.)/(Dry Wt.)

A suitable through-air-bonded-carded web material has a 2.5 osy (84.8 g/m$^2$) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb VERIGOOD white blotter paper available from Georgia Pacific Corporation, a business having offices located in Menasha, Wis., U.S.A. (e.g. product item number 411 01012). Substantially equivalent materials may optionally be employed.

The "menses simulant" test fluid is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed.

Gurley Stiffness Test Method

A suitable technique for determining the stiffness values described herein is a Gurley Stiffness test, a description of which is set forth in TAPPI Standard Test T 543 om-94 (Bending Resistance of Paper (Gurley-type tester)). A suitable testing apparatus is a Gurley Digital Stiffness Tester; Model 4171-E manufactured by Gurley Precision Instruments in Troy, N.Y. For purposes of the present invention, the stated Gurley stiffness values are intended to correspond to the values that would be generated by a "standard" size sample (1-inch by 1.5-inch). Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

Edge Compression Test Method

The method by which the Edge-wise Compression (EC) value can be determined is set forth below. A 2-inch by 12-inch (5.1 cm by 30.5 cm) piece of absorbent foam is used. The weight of the sample is determined. The thickness of the material is measured using a hand micrometer while avoiding surface compression. The material is formed into a cylinder having a height of 2 inches (5.1 cm), and with the two ends having 0–0.125 inch (0–3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

A tensile tester, such as those commercially available from MTS Systems Corporation in Eden Prairie, Minn., U.S.A., is configured with a bottom platform, a platen larger than the circumference of the sample to be tested and parallel to the bottom platform, attached to a compression load cell placed in the inverted position. The specimen is placed on the platform under the platen. The platen is brought into contact with the specimen and compresses the sample at a rate of 25 mm./min. The maximum force obtained in compressing the sample to 50% of its width (1 inch) (2.54 cm) is recorded.

Bucking of the material is identified as a maximum in the compression force and is typically observed before the material is compressed to 50% of its uncompressed length. In a product where the length of the absorbent is less than 12 inches (30.5 cm), the EC value of the material can be determined in the following manner. Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm). A detailed discussion of edge-wise compression strength has been given in *The Handbook Of Physical And Mechanical Testing Of Paper And Paperboard*, Richard E. Mark editor, Dekker 1983 (Vol. 1).

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A low-density, open-cell, thermoplastic, absorbent foam, comprising:
   a base resin, a surfactant, a plasticizing agent, and about 20% to about 50% by weight of a thermoplastic elastomer;
   wherein the foam has an open cell content of greater than 55% and a fluid intake flux of about 1 ml/sec/in$^2$ or greater upon a first insult, about 1 ml/sec/in² or greater upon a second insult, and about 1 ml/sec/in² or greater upon a third insult;

the foam is soft and flexible, and has a compression resistance of about 20% compression set or less; and the thermoplastic elastomer is selected from the group consisting of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS), polyolefin-based thermoplastic elastomers including ethylene α-olefin copolymers, hydrogenated butadiene-isoprene-butadiene block copolymers, stereoblock polypropylenes, ethylene-propylene-diene terpolymer (EPDM), ethylene-propylene random copolymers (EPM), ethylene propylene rubbers (EPR), thermoplastic polyether ester elastomers, ionomeric thermoplastic elastomers, polyamide thermoplastic elastomers, thermoplastic polyurethanes, and combinations thereof.

2. The foam of claim 1, wherein the base resin comprises at least one of the group consisting of polystyrene, styrene copolymers, polyolefins, polyesters, and combinations thereof.

3. The foam of claim 1, wherein the thermoplastic elastomer has a diblock content between about 50% and about 80% of a total weight of the thermoplastic elastomer.

4. The foam of claim 1, comprising between about 0.05% and about 10% surfactant, by weight, of the foam.

5. The foam of claim 1, wherein the surfactant comprises a nonionic surfactant.

6. The foam of claim 1, wherein the surfactant comprises a multi-component surfactant system.

7. The foam of claim 1, comprising between about 0.5% and about 10% plasticizing agent, by weight, of the foam.

8. The foam of claim 1, wherein the plasticizing agent comprises at least one of the group consisting of polyethylene; ethylene vinyl acetate; mineral oil, palm oil, waxes, naphthalene oil, paraffin oil, acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; 3-(2-xenoyl)-1,2-epoxypropane; and combinations thereof.

9. The foam of claim 1, wherein the foam has a density of about 0.1 g/cm³ or less.

10. The foam of claim 1, wherein the foam has an open-cell content of about 70% or greater.

11. The foam of claim 1, wherein the foam surfactant permanence remains intact in the foam such that a supernatant resulting from soaking the foam in water for 24 hours has a surface tension of about 40 dynes/centimeter or greater.

12. The foam of claim 1, wherein the foam has a saturated capacity of about 3 grams/gram or greater, as measured under a 0.5 psi loading.

13. The foam of claim 1, wherein the foam has a basis weight of about 400 grams per square meter or less.

14. The foam of claim 1, wherein the foam has an overall bulk of about 6 millimeters or less.

15. The foam of claim 1, wherein the foam has a cross-direction trap tear strength of about 300 grams or greater.

16. The foam of claim 1, wherein the foam has a machine-direction trap tear strength of about 300 grams or greater.

17. The foam of claim 1, wherein the foam has a Gurley stiffness of about 600 milligrams or less.

18. The foam of claim 1, wherein the foam has an edge compression of about 250 grams or less.

19. The foam of claim 1, wherein the foam has a compression resistance of about 20% compression set or less.

20. The foam of claim 1, wherein the foam has a vertical wicking height of about 5 cm or greater.

21. The foam of claim 1, wherein the foam has a viscous fluid saturation capacity of about 3 g/g or greater and retention capacity of about 1 g/g or greater.

22. An absorbent article comprising the foam of claim 1.

23. A soft, flexible, resilient, elastic, low-density, open-cell, thermoplastic, absorbent foam, comprising:

a base resin, about 20% to about 50% by weight of a thermoplastic elastomer, and a surfactant;

wherein the foam has an open cell content of greater than 55% and a fluid intake flux of about 1 ml/sec/in² or greater upon a first insult, about 1 ml/sec/in² or greater upon a second insult, and about 1 ml/sec/in² or greater upon a third insult;

the foam is soft and flexible, and has a compression resistance of about 20% compression set or less; and the thermoplastic elastomer is selected from the group consisting of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS), polyolefin-based thermoplastic elastomers including ethylene α-olefin copolymers, hydrogenated butadiene-isoprene-butadiene block copolymers, stereoblock polypropylenes, ethylene-propylene-diene terpolymer (EPDM), ethylene-propylene random copolymers (EPM), ethylene propylene rubbers (EPR), thermoplastic polyether ester elastomers, ionomeric thermoplastic elastomers, polyamide thermoplastic elastomers, thermoplastic polyurethanes, and combinations thereof.

24. The foam of claim 23, wherein the base resin comprises at least one of the group consisting of polystyrene, styrene copolymers, polyolefins, polyesters, and combinations thereof.

25. The foam of claim 23, wherein the thermoplastic elastomer comprises a styrenic block copolymer including at least one of the group consisting of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS), and combinations thereof.

26. The foam of claim 23, wherein the thermoplastic elastomer has a diblock content between about 50% and about 80% of a total weight of the thermoplastic elastomer.

27. The foam of claim 23, wherein the surfactant comprises a multi-component surfactant system.

28. The foam of claim 23, comprising between about 50% and about 90% base resin, by weight, of the foam.

29. The foam of claim 23, comprising between about 0.1% and about 5% surfactant, by weight, of the foam.

30. The foam of claim 23, wherein the foam has a density of about 0.1 g/cm³ or less, a Gurley stiffness of about 300 milligrams or less, and an edge compression of about 35 grams or less.

31. An absorbent article comprising the foam of claim 23.

32. A soft, flexible, resilient, elastic, low-density, open-cell, thermoplastic, absorbent foam, comprising:

between about 50% and 90% by weight, of a polystyrene base resin and between about 20% and about 50%, by weight, of a thermoplastic elastomer, wherein the thermoplastic elastomer has a styrenic block copolymer thermoplastic elastomer diblock content between about 50% and about 80% of a total weight of the thermoplastic elastomer;

wherein the foam has an open cell content of greater than 55% and a fluid intake flux of about 1 ml/sec/in$^2$ or greater upon a first insult, about 1 ml/sec/in$^2$ or greater upon a second insult, and about 1 ml/sec/in$^2$ or greater upon a third insult;

the foam is soft and flexible, and has a compression resistance of about 20% compression set or less; and the thermoplastic elastomer is selected from the group consisting of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS), polyolefin-based thermoplastic elastomers including ethylene α-olefin copolymers, hydrogenated butadiene-isoprene-butadiene block copolymers, stereoblock polypropylenes, ethylene-propylene-diene terpolymer (EPDM), ethylene-propylene random copolymers (EPM), ethylene propylene rubbers (EPR), thermoplastic polyether ester elastomers, ionomeric thermoplastic elastomers, polyamide thermoplastic elastomers, thermoplastic polyurethanes, and combinations thereof.

33. A method for producing a low-density, open-cell, thermoplastic, flexible, soft, absorbent foam, comprising the steps of:

providing a foam polymer formula including a base resin, a plasticizing agent, a surfactant and about 20% to about 50% by weight of a thermoplastic elastomer;

heating the foam polymer formula to create a polymer melt utilizing a blowing agent;

foaming the polymer melt to a density of about 0.1 g/cm$^3$ or less; and extruding the polymer melt to form an open-cell, soft, flexible, thermoplastic, absorbent foam;

wherein the foam has an open cell content of greater than 55% and a fluid intake flux of about 1 ml/sec/in$^2$ or greater upon a first insult, about 1 ml/sec/in$^2$ or greater upon a second insult, and about 1 ml/sec/in$^2$ or greater upon a third insult;

the foam is soft and flexible, and has a compression resistance of about 20% compression set or less; and the thermoplastic elastomer is selected from the group consisting of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS), polyolefin-based thermoplastic elastomers including ethylene α-olefin copolymers, hydrogenated butadiene-isoprene-butadiene block copolymers, stereoblock polypropylenes, ethylene-propylene-diene terpolymer (EPDM), ethylene-propylene random copolymers (EPM), ethylene propylene rubbers (EPR), thermoplastic polyether ester elastomers, ionomeric thermoplastic elastomers, polyamide thermoplastic elastomers, thermoplastic polyurethanes, and combinations thereof.

* * * * *

UNITED STATES PATENT AND TRADEMARK OFFICE
CERTIFICATE OF CORRECTION

PATENT NO. : 7,358,282 B2  
APPLICATION NO. : 10/729881  
DATED : April 15, 2008  
INVENTOR(S) : Krueger et al.

Page 1 of 1

It is certified that error appears in the above-identified patent and that said Letters Patent is hereby corrected as shown below:

In the Specification, column 8, line 50, delete "25 µg or greater" and insert therefor -- 25 g/g or greater --.

In the Specification, column 8, beginning on line 51, delete "3 µg or greater" and insert therefor -- 3 g/g or greater --.

In the Specification, column 28, line 46, delete "(e.g., four grains)" and insert therefor -- (e.g., four grams) --.

Signed and Sealed this

Twenty-third Day of June, 2009

JOHN DOLL  
*Acting Director of the United States Patent and Trademark Office*